United States Patent
Hong et al.

(10) Patent No.: US 9,605,043 B2
(45) Date of Patent: Mar. 28, 2017

(54) FUSION PROTEIN FOR SUPPRESSING CANCER CELL GROWTH AND SUPPRESSING VASCULOGENESIS, AND ANTICANCER COMPOSITION COMPRISING SAME

(75) Inventors: Hyo Jeong Hong, Seoul (KR); Rohit Singh, Gangwon-do (KR)

(73) Assignee: GENEONE LIFE SCIENCE, INC., Seoul (KR)

( * ) Notice: Subject to any disclaimer, the term of this patent is extended or adjusted under 35 U.S.C. 154(b) by 105 days.

(21) Appl. No.: 14/125,021

(22) PCT Filed: Jun. 8, 2012

(86) PCT No.: PCT/KR2012/004531
§ 371 (c)(1),
(2), (4) Date: Jan. 29, 2014

(87) PCT Pub. No.: WO2012/169822
PCT Pub. Date: Dec. 13, 2012

(65) Prior Publication Data
US 2014/0213769 A1    Jul. 31, 2014

(30) Foreign Application Priority Data

Jun. 10, 2011  (KR) .................. 10-2011-0056089
Jun. 7, 2012   (KR) .................. 10-2012-0061054

(51) Int. Cl.
| | |
|---|---|
| A61K 38/18 | (2006.01) |
| C07K 14/71 | (2006.01) |
| C07K 14/475 | (2006.01) |
| C07K 16/28 | (2006.01) |
| C07K 16/32 | (2006.01) |
| C07K 14/52 | (2006.01) |
| A61K 38/17 | (2006.01) |
| A61K 39/00 | (2006.01) |
| A61K 38/00 | (2006.01) |

(52) U.S. Cl.
CPC ............ *C07K 14/475* (2013.01); *C07K 14/52* (2013.01); *C07K 16/2863* (2013.01); *C07K 16/32* (2013.01); *A61K 38/00* (2013.01); *A61K 38/179* (2013.01); *A61K 2039/505* (2013.01); *C07K 2317/24* (2013.01); *C07K 2317/622* (2013.01); *C07K 2317/73* (2013.01); *C07K 2319/30* (2013.01); *C07K 2319/32* (2013.01)

(58) Field of Classification Search
None
See application file for complete search history.

(56) References Cited

U.S. PATENT DOCUMENTS

| | | | |
|---|---|---|---|
| 2003/0017977 A1 | 1/2003 | Xia et al. | |
| 2006/0153860 A1 | 7/2006 | Cho et al. | |
| 2007/0224203 A1 | 9/2007 | Friess et al. | |
| 2007/0244032 A1 | 10/2007 | Kim et al. | |
| 2010/0055093 A1 | 3/2010 | Shepard et al. | |

FOREIGN PATENT DOCUMENTS

| | | |
|---|---|---|
| KR | 10-2002-0019070 A | 3/2002 |
| KR | 10-2005-0045727 A | 5/2005 |
| KR | 10-2007-0034512 A | 3/2007 |
| KR | 10-2008-0096598 A | 10/2008 |
| KR | 10-2009-0031897 A | 3/2009 |

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
International Searching Authority, International Search Report of PCT/KR2012/004531, dated Dec. 3, 2012.
Xiao-Feng Le, et al., "Specific blockade of VEGF and HER2 pathways results in greater growth inhibition of breast cancer xenografts that overexpress HER2", Cell Cycle, Landes Bioscience, Dec. 1, 2008, pp. 3747-3758, vol. 7, Issue 23.
Seung-Uon Shin et al., "Molecular Cancer Therapeutics", Targeted Delivery of an Antibody-Mutant Human Endostatin Fusion Protein Results in Enhanced Antitumor Efficacy, pp. 603-614, Mar. 10, 2011, DOI: 10.1158/1535-7163. MCT-10-0804.
Korean Patent Office; Korean Office Action issued Nov. 22, 2013 in corresponding Korean Application No. 10-2012-0061054.
Korean Intellectual Property Office, Communication dated May 10, 2014, issued in corresponding Korean Application No. 10-2012-0061054.
Le et al., "Specific blockade of VEGF and HER2 pathways results in greater growth inhibition of breast cancer xenografts that overexpress HER2", Cell Cycle, Landes Bioscience, Dec. 1, 2008, vol. 7, Issue 23, pp. 3747-3758.
Tsai et al., "Enhancement of antitumor immune response by targeted interleukin-12 electrogene transfer through antiHER2 single-chain antibody in a murine bladder tumor model", Vaccine, Elsevier Ltd., Jul. 9, 2009, vol. 27, pp. 5383-5392.

(Continued)

*Primary Examiner* — Christine J Saoud
*Assistant Examiner* — Jon M Lockard
(74) *Attorney, Agent, or Firm* — Sughrue Mion, PLLC

(57) ABSTRACT

The present invention relates to a fusion protein resulting from the fusion of a cancer-specific antibody and an angiogenesis inhibitor, and relates to an anti-cancer composition including the same. More specifically, in the present invention, it is preferable that the cancer-specific antibody is trastuzumab or a fragment thereof, and the angiogenesis inhibitor is a VEGF-Trap. When the fusion protein according to the present invention is used, there are advantages in that angiogenesis and cancer cell growth can be effectively inhibited as compared to trastuzumab or VEGF-Trap, and side effects can also be reduced.

3 Claims, 15 Drawing Sheets

(56) References Cited

OTHER PUBLICATIONS

Stains et al., "A General Approach for Receptor and Antibody-Targeted Detection of Native Proteins Utilizing Split-Luciferase Reassembly", ACS Chemical Biology, Jul. 23, 2010, vol. 5, No. 10, pp. 943-952.

\* cited by examiner

FIG. 1
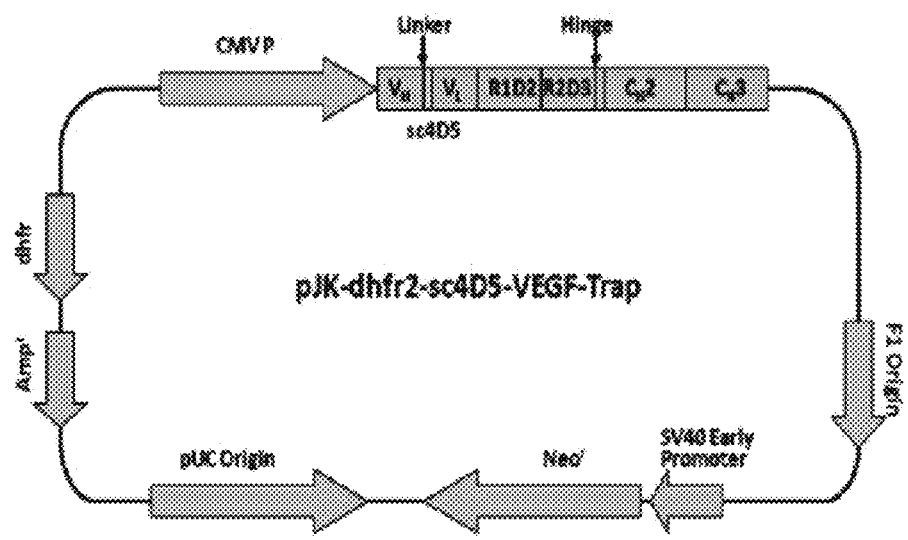
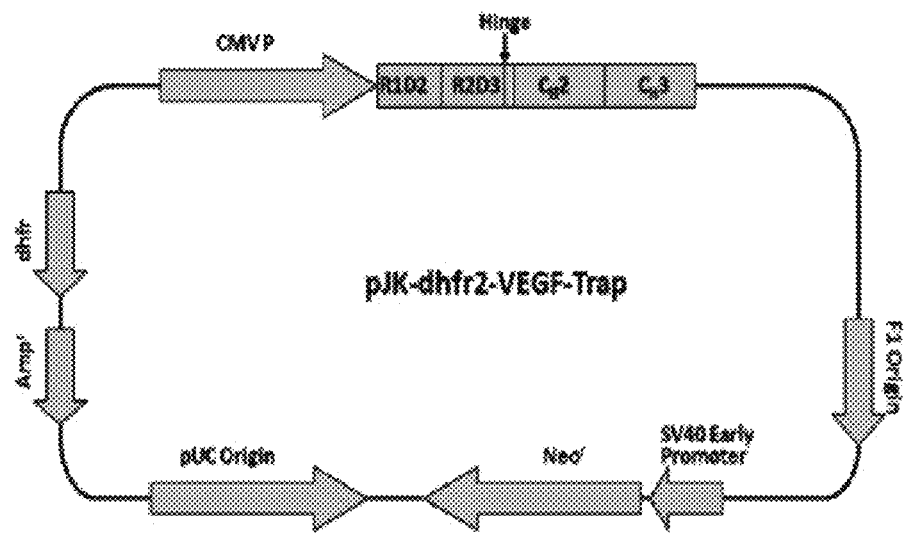

FIG. 2
A
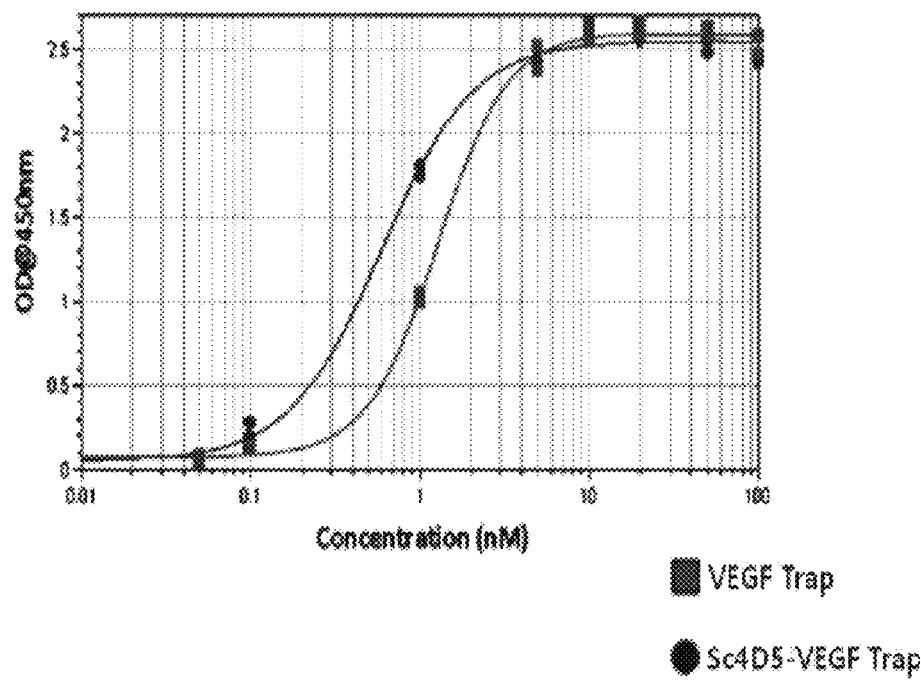
■ VEGF Trap
● Sc4D5-VEGF Trap
B
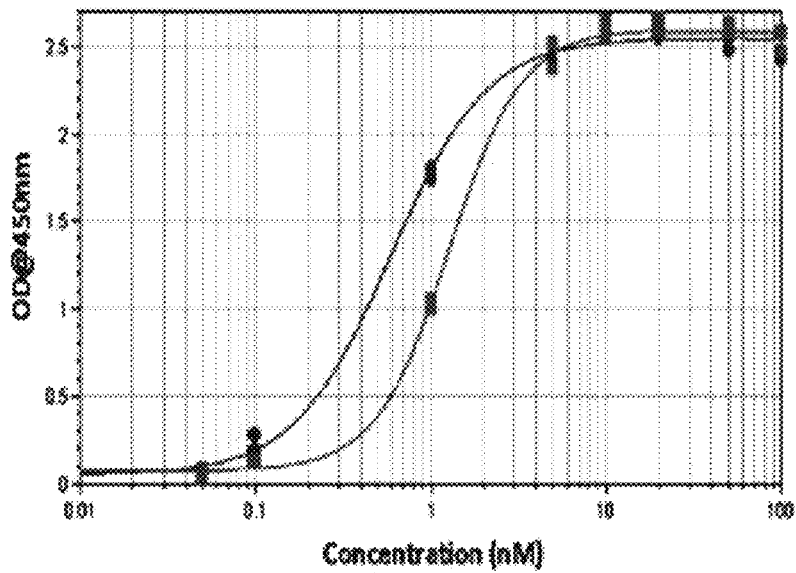

FIG. 6
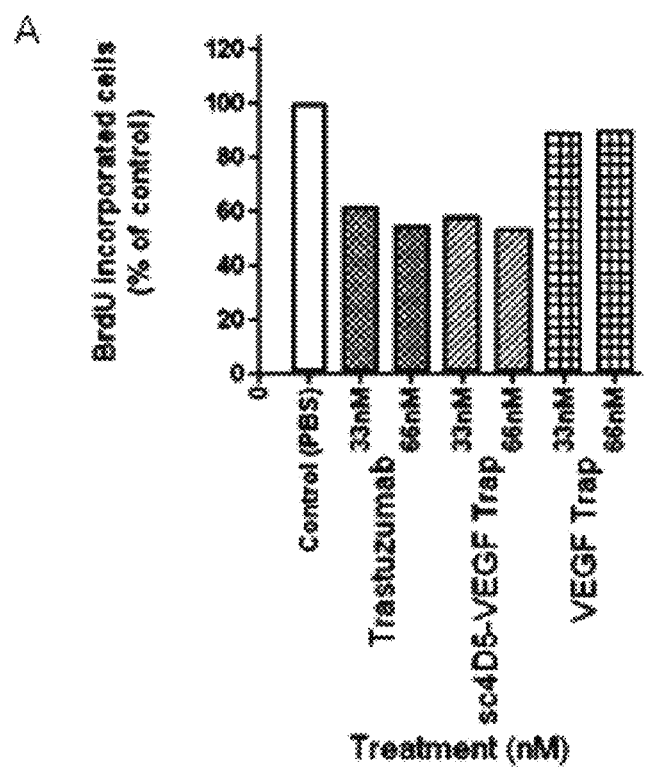
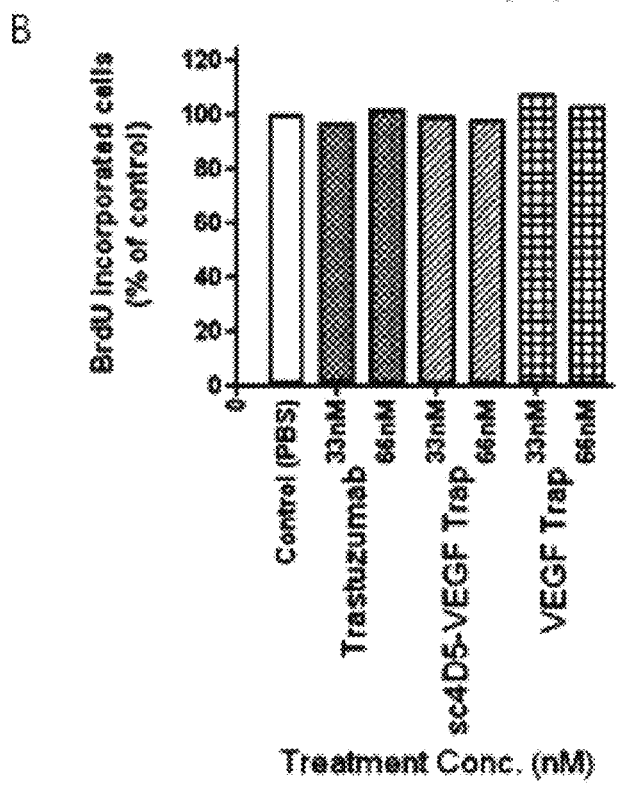

Lane1: sc4D5-VEGF Trap
Lane2: sc4D5-R2D2D3-hFc
Lane3: Protein Marker
Lane4: sc4D5-VEGF Trap
Lane5 sc4D5-R2D2D3-hFc

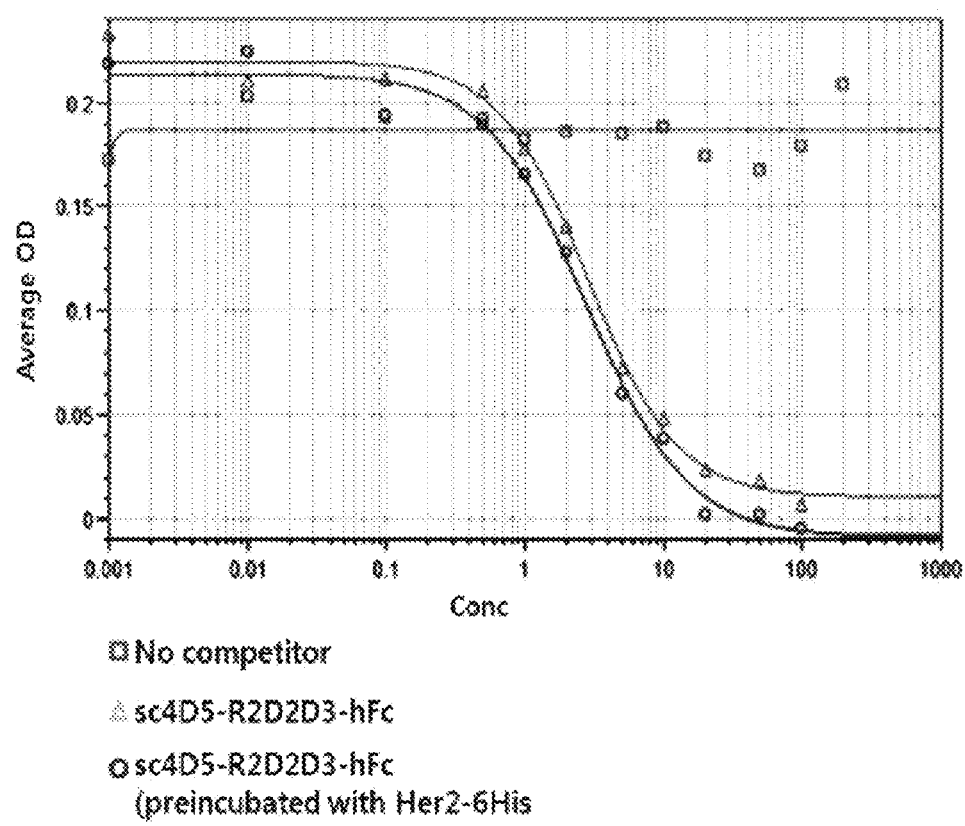

SEQUENCE LISTING

```
<160> NUMBER OF SEQ ID NOS: 25

<210> SEQ ID NO 1
<211> LENGTH: 432
<212> TYPE: PRT
<213> ORGANISM: Artificial Sequence
<220> FEATURE:
<223> OTHER INFORMATION: Description of Artificial Sequence: Synthetic
      VEGF-trap(Fc) 1 polypeptide

<400> SEQUENCE: 1

Gly Arg Pro Phe Val Glu Met Tyr Ser Glu Ile Pro Glu Ile Ile His
1               5                   10                  15

Met Thr Glu Gly Arg Glu Leu Val Ile Pro Cys Arg Val Thr Ser Pro
            20                  25                  30

Asn Ile Thr Val Thr Leu Lys Lys Phe Pro Leu Asp Thr Leu Ile Pro
        35                  40                  45

Asp Gly Lys Arg Ile Ile Trp Asp Ser Arg Lys Gly Phe Ile Ile Ser
    50                  55                  60

Asn Ala Thr Tyr Lys Glu Ile Gly Leu Leu Thr Cys Glu Ala Thr Val
65                  70                  75                  80
```

```
Asn Gly His Leu Tyr Lys Thr Asn Tyr Leu Thr His Arg Gln Thr Asn
             85                  90                  95

Thr Ile Ile Asp Val Val Leu Ser Pro Ser His Gly Ile Glu Leu Ser
            100                 105                 110

Val Gly Glu Lys Leu Val Leu Asn Cys Thr Ala Arg Thr Glu Leu Asn
            115                 120                 125

Val Gly Ile Asp Phe Asn Trp Glu Tyr Pro Ser Ser Lys His Gln His
            130                 135                 140

Lys Lys Leu Val Asn Arg Asp Leu Lys Thr Gln Ser Gly Ser Glu Met
145                 150                 155                 160

Lys Lys Phe Leu Ser Thr Leu Thr Ile Asp Gly Val Thr Arg Ser Asp
                165                 170                 175

Gln Gly Leu Tyr Thr Cys Ala Ala Ser Ser Gly Leu Met Thr Lys Lys
                180                 185                 190

Asn Ser Thr Phe Val Arg Val His Glu Lys Gly Pro Gly Asp Lys Thr
                195                 200                 205

His Thr Cys Pro Pro Cys Pro Ala Pro Glu Leu Leu Gly Gly Pro Ser
            210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
                260                 265                 270

Lys Thr Lys Pro Arg Glu Glu Gln Tyr Asn Ser Thr Tyr Arg Val Val
                275                 280                 285

Ser Val Leu Thr Val Leu His Gln Asp Trp Leu Asn Gly Lys Glu Tyr
            290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
                325                 330                 335

Pro Pro Ser Arg Asp Glu Leu Thr Lys Asn Gln Val Ser Leu Thr Cys
                340                 345                 350

Leu Val Lys Gly Phe Tyr Pro Ser Asp Ile Ala Val Glu Trp Glu Ser
                355                 360                 365

Asn Gly Gln Pro Glu Asn Asn Tyr Lys Thr Thr Pro Pro Val Leu Asp
            370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
                405                 410                 415

Leu His Asn His Tyr Thr Gln Lys Ser Leu Ser Leu Ser Pro Gly Lys
                420                 425                 430

<210> SEQ ID NO 2
<211> LENGTH: 120
<212> TYPE: PRT
<213> ORGANISM: Artificial Sequence
<220> FEATURE:
<223> OTHER INFORMATION: Description of Artificial Sequence: Synthetic
      scFv heavy chain variable region polypeptide

<400> SEQUENCE: 2

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
            115                 120

<210> SEQ ID NO 3
<211> LENGTH: 108
<212> TYPE: PRT
<213> ORGANISM: Artificial Sequence
<220> FEATURE:
<223> OTHER INFORMATION: Description of Artificial Sequence: Synthetic
      scFv light chain variable region polypeptide

<400> SEQUENCE: 3

Asp Ile Gln Met Thr Gln Ser Pro Ser Ser Leu Ser Ala Ser Val Gly
 1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg
            100                 105

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 4

Gly Gly Gly Gly Ser Gly Gly Gly Gly Ser Gly Gly Gly Gly Ser
 1               5                   10                  15

<210> SEQ ID NO 5
<211> LENGTH: 243
<212> TYPE: PRT
<213> ORGANISM: Artificial Sequence
<220> FEATURE:
<223> OTHER INFORMATION: Description of Artificial Sequence: Synthetic
      sc4D5 polypeptide

<400> SEQUENCE: 5
```

-continued

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asn Ile Lys Asp Thr
             20                  25                  30

Tyr Ile His Trp Val Arg Gln Ala Pro Gly Lys Gly Leu Glu Trp Val
         35                  40                  45

Ala Arg Ile Tyr Pro Thr Asn Gly Tyr Thr Arg Tyr Ala Asp Ser Val
     50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Ser Gly Gly Gly
            115                 120                 125

Gly Ser Gly Gly Gly Ser Asp Ile Gln Met Thr Gln Ser Pro Ser
            130                 135                 140

Ser Leu Ser Ala Ser Val Gly Asp Arg Val Thr Ile Thr Cys Arg Ala
145                 150                 155                 160

Ser Gln Asp Val Asn Thr Ala Val Ala Trp Tyr Gln Lys Pro Gly
                165                 170                 175

Lys Ala Pro Lys Leu Leu Ile Tyr Ser Ala Ser Phe Leu Tyr Ser Gly
                180                 185                 190

Val Pro Ser Arg Phe Ser Gly Ser Arg Ser Gly Thr Asp Phe Thr Leu
                195                 200                 205

Thr Ile Ser Ser Leu Gln Pro Glu Asp Phe Ala Thr Tyr Tyr Cys Gln
        210                 215                 220

Gln His Tyr Thr Thr Pro Pro Thr Phe Gly Gln Gly Thr Lys Val Glu
225                 230                 235                 240

Ile Lys Arg

<210> SEQ ID NO 6
<211> LENGTH: 448
<212> TYPE: PRT
<213> ORGANISM: Artificial Sequence
<220> FEATURE:
<223> OTHER INFORMATION: Description of Artificial Sequence: Synthetic
      sc4D5-VEGF-trap 1 fusion polypeptide

<400> SEQUENCE: 6

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asn Ile Lys Asp Thr
             20                  25                  30

Tyr Ile His Trp Val Arg Gln Ala Pro Gly Lys Gly Leu Glu Trp Val
         35                  40                  45

Ala Arg Ile Tyr Pro Thr Asn Gly Tyr Thr Arg Tyr Ala Asp Ser Val
     50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110
```

```
Gly Thr Leu Val Thr Val Ser Gly Gly Gly Ser Gly Gly
        115                 120                 125

Gly Ser Gly Gly Gly Ser Asp Ile Gln Met Thr Gln Ser Pro Ser
130                 135                 140

Ser Leu Ser Ala Ser Val Gly Asp Arg Val Thr Ile Thr Cys Arg Ala
145                 150                 155                 160

Ser Gln Asp Val Asn Thr Ala Val Ala Trp Tyr Gln Gln Lys Pro Gly
                165                 170                 175

Lys Ala Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
210                 215                 220

Gln His Tyr Thr Thr Pro Pro Thr Phe Gly Gln Gly Thr Lys Val Glu
225                 230                 235                 240

Ile Lys Arg Gly Arg Pro Phe Val Glu Met Tyr Ser Glu Ile Pro Glu
                245                 250                 255

Ile Ile His Met Thr Glu Gly Arg Glu Leu Val Ile Pro Cys Arg Val
            260                 265                 270

Thr Ser Pro Asn Ile Thr Val Thr Leu Lys Lys Phe Pro Leu Asp Thr
        275                 280                 285

Leu Ile Pro Asp Gly Lys Arg Ile Ile Trp Asp Ser Arg Lys Gly Phe
290                 295                 300

Ile Ile Ser Asn Ala Thr Tyr Lys Glu Ile Gly Leu Leu Thr Cys Glu
305                 310                 315                 320

Ala Thr Val Asn Gly His Leu Tyr Lys Thr Asn Tyr Leu Thr His Arg
                325                 330                 335

Gln Thr Asn Thr Ile Ile Asp Val Val Leu Ser Pro Ser His Gly Ile
            340                 345                 350

Glu Leu Ser Val Gly Glu Lys Leu Val Leu Asn Cys Thr Ala Arg Thr
        355                 360                 365

Glu Leu Asn Val Gly Ile Asp Phe Asn Trp Glu Tyr Pro Ser Ser Lys
370                 375                 380

His Gln His Lys Lys Leu Val Asn Arg Asp Leu Lys Thr Gln Ser Gly
385                 390                 395                 400

Ser Glu Met Lys Lys Phe Leu Ser Thr Leu Thr Ile Asp Gly Val Thr
                405                 410                 415

Arg Ser Asp Gln Gly Leu Tyr Thr Cys Ala Ala Ser Ser Gly Leu Met
            420                 425                 430

Thr Lys Lys Asn Ser Thr Phe Val Arg Val His Glu Lys Gly Pro Gly
        435                 440                 445
```

<210> SEQ ID NO 7
<211> LENGTH: 19
<212> TYPE: PRT
<213> ORGANISM: Artificial Sequence
<220> FEATURE:
<223> OTHER INFORMATION: Description of Artificial Sequence: Synthetic leader region peptide

<400> SEQUENCE: 7

```
Met Glu Trp Ser Trp Val Phe Leu Phe Phe Leu Ser Val Thr Thr Gly
1               5                   10                  15

Val His Ser
```

<210> SEQ ID NO 8
<211> LENGTH: 729
<212> TYPE: DNA
<213> ORGANISM: Artificial Sequence
<220> FEATURE:
<223> OTHER INFORMATION: Description of Artificial Sequence: Synthetic scFv polynucleotide

<400> SEQUENCE: 8

```
gaggtgcagc tggtggaaag cggcggaggc ctggtgcagc tggcggaag cctgagactg      60
agctgtgccg ccagcggctt caacatcaag gacacctaca tccactgggt ccgacaggcc    120
cctggcaagg gcctggaatg ggtggcccgg atctaccca ccaacggcta caccagatac     180
gccgacagcg tgaagggccg gttcaccatc agcgccgaca ccagcaagaa caccgcctac    240
ctgcagatga acagcctgcg ggccgaggac accgccgtgt actactgcag cagatgggga    300
ggcgacggct ctacgccat ggactactgg ggccagggca cctggtcac cgtgtctagc      360
ggaggcggcg gatctggcgg cggaggaagt ggcggaggcg gaagcgacat ccagatgacc    420
cagagcccca gcagcctgag cgccagcgtg ggcgacagag tgaccatcac ctgtcgggcc    480
agccaggacg tgaacacagc cgtggcctgg tatcagcaga agcccggcaa ggccccaag    540
ctgctgatct acagcgccag cttcctgtac agcggcgtgc ccagccggtt cagcggcagc    600
agaagcggca ccgacttcac cctgaccatc tccagcctgc agcccgagga tttcgccacc    660
tactattgcc agcagcacta caccaccccc cccaccttcg gacagggcac caaggtggaa    720
atcaagcgc                                                            729
```

<210> SEQ ID NO 9
<211> LENGTH: 1299
<212> TYPE: DNA
<213> ORGANISM: Artificial Sequence
<220> FEATURE:
<223> OTHER INFORMATION: Description of Artificial Sequence: Synthetic VEGF-trap(Fc) 1 polynucleotide

<400> SEQUENCE: 9

```
ggccgcccct tcgtggaaat gtacagcgag atccccgaga tcatccacat gaccgagggc     60
agagagctgg tcatcccctg cagagtgacc tcccccaaca tcaccgtgac cctgaagaag    120
ttccccctgg acaccctgat ccccgacggc aagcggatca tctgggacag ccggaagggc    180
ttcatcatca gcaacgccac ctacaaagag atcgggctgc tgacctgcga ggccaccgtg    240
aacggccacc tgtacaagac caactacctg acccaccggc agaccaacac catcatcgac    300
gtggtgctga gccccagcca cggcatcgag ctgtccgtgg gcgagaagct ggtgctgaac    360
tgcaccgccc ggaccgagct gaacgtgggc atcgacttca ctgggagta ccccagcagc    420
aagcaccagc acaagaagct ggtcaaccgg gacctgaaaa cccagagcgg cagcgagatg    480
aagaagtttc tgagcaccct gacaatcgac ggcgtgacca agagcgacca gggcctgtac    540
acatgcgccg ccagcagcgg cctgatgacc aagaaaaaca gcaccttcgt gcgggtgcac    600
gagaagggac ccggcgacaa gacccacacc tgtcccccctt gccctgcccc tgagctgctg    660
ggaggccctt ccgtgtttct gttccccca aagcccaagg ataccctgat gatcagccgg    720
acccccgaag tgacctgcgt ggtggtggac gtgtcccacg aggaccctga agtgaagttc    780
aattggtacg tggacggcgt ggaagtgcac aacgccaaga ccaagccag agaggaacag    840
tacaacagca cctaccgggt ggtgtccgtg ctgaccgtgc tgcaccagga ctggctgaac    900
ggcaaagagt acaagtgcaa ggtctccaac aaggccctgc ctgccccat cgagaaaacc    960
```

```
atcagcaagg ccaagggcca gccccgcgag cctcaggtgt acacactgcc ccccagccgg    1020
gacgagctga ccaagaacca ggtgtccctg acctgcctgg tcaagggctt ctaccccagc    1080
gatatcgccg tggaatggga gagcaacggc cagcccgaga caactacaa gaccacccct     1140 cccgtgctgg acagcgacgg ctcattcttc ctgtactcca agctgaccgt ggacaagagc    1200
cggtggcagc agggcaacgt gttcagctgc agcgtgatgc acgaggccct gcacaaccac    1260
tacacccaga gtccctgag cctgagcccc ggcaaatga                             1299
```

```
<210> SEQ ID NO 10
<211> LENGTH: 2028
<212> TYPE: DNA
<213> ORGANISM: Artificial Sequence
<220> FEATURE:
<223> OTHER INFORMATION: Description of Artificial Sequence: Synthetic
      sc4D5-VEGF-trap(Fc) 1 fusion polynucleotide

<400> SEQUENCE: 10
```

```
gaggtgcagc tggtggaaag cggcggaggc ctggtgcagc tggcggaag cctgagactg      60 agctgtgccg ccagcggctt caacatcaag gacacctaca tccactgggt ccgacaggcc    120
cctggcaagg gcctggaatg ggtggcccgg atctaccccca caacggcta caccagatac    180 gccgacagcg tgaagggccg gttcaccatc agcgccgaca ccagcaagaa caccgcctac    240
ctgcagatga acagcctgcg ggccgaggac accgccgtgt actactgcag cagatgggga    300
ggcgacggct tctacgccat ggactactgg ggccagggca ccctggtcac cgtgtctagc    360
ggaggcggcg gatctggcgg cggaggaagt ggcggaggcg gaagcgacat ccagatgacc    420
cagagcccca gcagcctgag cgccagcgtg ggcgacagag tgaccatcac ctgtcgggcc    480
agccaggacg tgaacacagc cgtggcctgg tatcagcaga agcccggcaa ggccccaag    540 ctgctgatct acagcgccag cttcctgtac agcggcgtgc ccagccggtt cagcggcagc    600
agaagcggca ccgacttcac cctgaccatc tccagcctgc agcccgagga tttcgccacc    660
tactattgcc agcagcacta ccaccacccc cccaccttcg gacagggcac caaggtggaa    720
atcaagcgcg ccgccccttt cgtggaaatg tacagcgaga tccccgagat catccacatg    780
accgagggca gagagctggt catcccctgc agagtgaccct cccccaacat caccgtgacc    840
ctgaagaagt tccccctgga cacctgatc ccgacggca gcggatcat ctgggacagc    900 cggaagggct tcatcatcag caacgccacc tacaaagaga tcgggctgct gacctgcgag    960
gccaccgtga acggccacct gtacaagacc aactacctga cccaccggca gaccaacacc    1020
atcatcgacg tggtgctgag ccccagccac ggcatcgagc tgtccgtggg cgagaagctg    1080
gtgctgaact gcaccgcccg gaccgagctg aacgtgggca tcgacttcaa ctgggagtac    1140
cccagcagca agcaccagca caagaagctg gtcaaccggg acctgaaaac ccagagcggc    1200
agcgagatga agaagtttct gagcaccctg acaatcgacg gcgtgaccag aagcgaccag    1260
ggcctgtaca catgcgccgc cagcagcggc ctgatgacca agaaaaacag caccttcgtg    1320
cgggtgcacg agaagggacc cggcgacaag acccacacct gtccccttg ccctgcccct    1380 gagctgctgg gaggcccttc cgtgtttctg ttccccccaa agcccaagga tacccctgatg    1440 atcagccgga cccccgaagt gacctgcgtg gtggtggacg tgtcccacga ggaccctgaa    1500
gtgaagttca attggtacgt ggacggcgtg gaagtgcaca acgccaagac caagcccaga    1560
gaggaacagt acaacagcac ctaccgggtg gtgtccgtgc tgaccgtgct gcaccaggac    1620
tggctgaacg gcaaagagta caagtgcaag gtctccaaca aggccctgcc tgcccccatc    1680
```

-continued

```
gagaaaacca tcagcaaggc caagggccag ccccgcgagc ctcaggtgta cacactgccc   1740
cccagccggg acgagctgac caagaaccag gtgtccctga cctgcctggt caagggcttc   1800
taccccagcg atatcgccgt ggaatgggag agcaacggcc agcccgagaa caactacaag   1860 accaccccctc ccgtgctgga cagcgacggc tcattcttcc tgtactccaa gctgaccgtg   1920
gacaagagcc ggtggcagca gggcaacgtg ttcagctgca gcgtgatgca cgaggccctg   1980
cacaaccact acacccagaa gtccctgagc ctgagccccg gcaaatga             2028
```

<210> SEQ ID NO 11
<211> LENGTH: 57
<212> TYPE: DNA
<213> ORGANISM: Artificial Sequence
<220> FEATURE:
<223> OTHER INFORMATION: Description of Artificial Sequence: Synthetic leader oligonucleotide

<400> SEQUENCE: 11

```
atggaatggt cctgggtgtt cctgttcttc ctgagcgtga ccaccggcgt gcacagc           57
```

<210> SEQ ID NO 12
<211> LENGTH: 442
<212> TYPE: PRT
<213> ORGANISM: Artificial Sequence
<220> FEATURE:
<223> OTHER INFORMATION: Description of Artificial Sequence: Synthetic VEGF-trap(Fc) 2 polypeptide

<400> SEQUENCE: 12

```
Gly Arg Tyr Val Gln Asp Tyr Arg Ser Pro Phe Ile Ala Ser Val Ser
1               5                   10                  15

Asp Gln His Gly Val Val Tyr Ile Thr Glu Asn Lys Asn Lys Thr Val
            20                  25                  30

Val Ile Pro Cys Leu Gly Ser Ile Ser Asn Leu Asn Val Ser Leu Cys
        35                  40                  45

Ala Arg Tyr Pro Glu Lys Arg Phe Val Pro Asp Gly Asn Arg Ile Ser
    50                  55                  60

Trp Asp Ser Lys Lys Gly Phe Thr Ile Pro Ser Tyr Met Ile Ser Tyr
65                  70                  75                  80

Ala Gly Met Val Phe Cys Glu Ala Lys Ile Asn Asp Glu Ser Tyr Gln
                85                  90                  95

Ser Ile Met Tyr Ile Val Val Val Gly Tyr Arg Ile Asp Val Val
            100                 105                 110

Leu Ser Pro Ser His Gly Ile Glu Leu Ser Val Gly Glu Lys Leu Val
        115                 120                 125

Leu Asn Cys Thr Ala Arg Thr Glu Leu Asn Val Gly Ile Asp Phe Asn
    130                 135                 140

Trp Glu Tyr Pro Ser Ser Lys His Gln His Lys Lys Leu Val Asn Arg
145                 150                 155                 160

Asp Leu Lys Thr Gln Ser Gly Ser Glu Met Lys Lys Phe Leu Ser Thr
                165                 170                 175

Leu Thr Ile Asp Gly Val Thr Arg Ser Asp Gln Gly Leu Tyr Thr Cys
            180                 185                 190

Ala Ala Ser Ser Gly Leu Met Thr Lys Lys Asn Ser Thr Phe Val Arg
        195                 200                 205

Val His Glu Lys Gly Pro Gly Asp Lys Thr His Thr Cys Pro Pro Cys
    210                 215                 220
```

-continued

```
Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
            245                 250                 255

Val Val Val Asp Val Ser His Glu Asp Pro Glu Val Lys Phe Asn Trp
        260                 265                 270

Tyr Val Asp Gly Val Glu Val His Asn Ala Lys Thr Lys Pro Arg Glu
    275                 280                 285

Glu Gln Tyr Asn Ser Thr Tyr Arg Val Val Ser Val Leu Thr Val Leu
290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
            325                 330                 335

Gln Pro Arg Glu Pro Gln Val Tyr Thr Leu Pro Pro Ser Arg Asp Glu
        340                 345                 350

Leu Thr Lys Asn Gln Val Ser Leu Thr Cys Leu Val Lys Gly Phe Tyr
    355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
            405                 410                 415

Val Phe Ser Cys Ser Val Met His Glu Ala Leu His Asn His Tyr Thr
        420                 425                 430

Gln Lys Ser Leu Ser Leu Ser Pro Gly Lys
    435                 440

<210> SEQ ID NO 13
<211> LENGTH: 205
<212> TYPE: PRT
<213> ORGANISM: Artificial Sequence
<220> FEATURE:
<223> OTHER INFORMATION: Description of Artificial Sequence: Synthetic
      VEGF-trap 1 polypeptide

<400> SEQUENCE: 13

Gly Arg Pro Phe Val Glu Met Tyr Ser Glu Ile Pro Glu Ile Ile His
1               5                   10                  15

Met Thr Glu Gly Arg Glu Leu Val Ile Pro Cys Arg Val Thr Ser Pro
            20                  25                  30

Asn Ile Thr Val Thr Leu Lys Lys Phe Pro Leu Asp Thr Leu Ile Pro
        35                  40                  45

Asp Gly Lys Arg Ile Ile Trp Asp Ser Arg Lys Gly Phe Ile Ile Ser
    50                  55                  60

Asn Ala Thr Tyr Lys Glu Ile Gly Leu Leu Thr Cys Glu Ala Thr Val
65                  70                  75                  80

Asn Gly His Leu Tyr Lys Thr Asn Tyr Leu Thr His Arg Gln Thr Asn
                85                  90                  95

Thr Ile Ile Asp Val Val Leu Ser Pro Ser His Gly Ile Glu Leu Ser
            100                 105                 110

Val Gly Glu Lys Leu Val Leu Asn Cys Thr Ala Arg Thr Glu Leu Asn
        115                 120                 125

Val Gly Ile Asp Phe Asn Trp Glu Tyr Pro Ser Ser Lys His Gln His
    130                 135                 140
```

```
Lys Lys Leu Val Asn Arg Asp Leu Lys Thr Gln Ser Gly Ser Glu Met
145                 150                 155                 160

Lys Lys Phe Leu Ser Thr Leu Thr Ile Asp Gly Val Thr Arg Ser Asp
                165                 170                 175

Gln Gly Leu Tyr Thr Cys Ala Ala Ser Ser Gly Leu Met Thr Lys Lys
            180                 185                 190

Asn Ser Thr Phe Val Arg Val His Glu Lys Gly Pro Gly
        195                 200                 205

<210> SEQ ID NO 14
<211> LENGTH: 215
<212> TYPE: PRT
<213> ORGANISM: Artificial Sequence
<220> FEATURE:
<223> OTHER INFORMATION: Description of Artificial Sequence: Synthetic
      VEGF-trap 2 polypeptide

<400> SEQUENCE: 14

Gly Arg Tyr Val Gln Asp Tyr Arg Ser Pro Phe Ile Ala Ser Val Ser
1               5                   10                  15

Asp Gln His Gly Val Val Tyr Ile Thr Glu Asn Lys Asn Lys Thr Val
                20                  25                  30

Val Ile Pro Cys Leu Gly Ser Ile Ser Asn Leu Asn Val Ser Leu Cys
            35                  40                  45

Ala Arg Tyr Pro Glu Lys Arg Phe Val Pro Asp Gly Asn Arg Ile Ser
        50                  55                  60

Trp Asp Ser Lys Lys Gly Phe Thr Ile Pro Ser Tyr Met Ile Ser Tyr
65                  70                  75                  80

Ala Gly Met Val Phe Cys Glu Ala Lys Ile Asn Asp Glu Ser Tyr Gln
                85                  90                  95

Ser Ile Met Tyr Ile Val Val Val Gly Tyr Arg Ile Asp Val Val
                100                 105                 110

Leu Ser Pro Ser His Gly Ile Glu Leu Ser Val Gly Glu Lys Leu Val
            115                 120                 125

Leu Asn Cys Thr Ala Arg Thr Glu Leu Asn Val Gly Ile Asp Phe Asn
130                 135                 140

Trp Glu Tyr Pro Ser Ser Lys His Gln His Lys Lys Leu Val Asn Arg
145                 150                 155                 160

Asp Leu Lys Thr Gln Ser Gly Ser Glu Met Lys Lys Phe Leu Ser Thr
                165                 170                 175

Leu Thr Ile Asp Gly Val Thr Arg Ser Asp Gln Gly Leu Tyr Thr Cys
            180                 185                 190

Ala Ala Ser Ser Gly Leu Met Thr Lys Lys Asn Ser Thr Phe Val Arg
        195                 200                 205

Val His Glu Lys Gly Pro Gly
    210                 215

<210> SEQ ID NO 15
<211> LENGTH: 227
<212> TYPE: PRT
<213> ORGANISM: Homo sapiens
<220> FEATURE:
<223> OTHER INFORMATION: Fc region

<400> SEQUENCE: 15

Asp Lys Thr His Thr Cys Pro Pro Cys Pro Ala Pro Glu Leu Leu Gly
1               5                   10                  15
```

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys
225

<210> SEQ ID NO 16
<211> LENGTH: 1329
<212> TYPE: DNA
<213> ORGANISM: Artificial Sequence
<220> FEATURE:
<223> OTHER INFORMATION: Description of Artificial Sequence: Synthetic
      VEGF-trap(Fc) 2 polynucleotide

<400> SEQUENCE: 16
ggccgctacg tgcaggacta cagaagcccc tttatcgcca gcgtgtccga ccagcacggc      60
gtggtgtaca tcaccgagaa caagaacaag accgtggtga tccccctgcct gggcagcatc    120 agcaacctga acgtgtccct gtgcgccaga taccccgaga gagattcgt gcccgacggc      180 aaccggatca gctgggacag caagaagggc ttcaccatcc ccagctacat gatcagctac     240
gccggcatgg tgttctgcga ggccaagatc aacgacgaga gctaccagag catcatgtac     300
atcgtggtgg tggtgggata ccggatcgac gtggtgctga gccccagcca cggcatcgag     360
ctgtccgtgg gcgagaagct ggtgctgaac tgcaccgccc ggaccgagct gaacgtgggc     420
atcgacttca ctggagta ccccagcagc aagcaccagc acaagaagct ggtcaaccgg      480
gacctgaaaa cccagagcgg cagcgagatg aagaagtttc tgagcaccct gacaatcgac     540
ggcgtgacca aagcgacca gggcctgtac acatgcgccg ccagcagcgg cctgatgacc     600
aagaaaaaca gcacctctcgt gcgggtgcac gagaagggac ccggcgacaa gacccacacc    660
tgtccccctt gccctgcccc tgagctgctg ggaggcccct tcgtgtttct gttcccccca     720
aagcccaagg atacccctgat gatcagccgg accccgaag tgacctgcgt ggtggtggac    780

```
gtgtcccacg aggaccctga agtgaagttc aattggtacg tggacggcgt ggaagtgcac    840
aacgccaaga ccaagcccag agaggaacag tacaacagca cctaccgggt ggtgtccgtg    900
ctgaccgtgc tgcaccagga ctggctgaac ggcaaagagt acaagtgcaa ggtctccaac    960
aaggccctgc ctgcccccat cgagaaaacc atcagcaagg ccaagggcca gccccgcgag   1020
cctcaggtgt acacactgcc ccccagccgg gacgagctga ccaagaacca ggtgtccctg   1080
acctgcctgg tcaagggctt ctaccccagc gatatcgccg tggaatggga gagcaacggc   1140
cagcccgaga caactacaa gaccacccct cccgtgctgg acagcgacgg ctcattcttc    1200
ctgtactcca agctgaccgt ggacaagagc cggtggcagc agggcaacgt gttcagctgc   1260
agcgtgatgc acgaggccct gcacaaccac tacacccaga gtccctgag cctgagcccc    1320 ggcaaatga                                                           1329
```

<210> SEQ ID NO 17
<211> LENGTH: 615
<212> TYPE: DNA
<213> ORGANISM: Artificial Sequence
<220> FEATURE:
<223> OTHER INFORMATION: Description of Artificial Sequence: Synthetic
      VEGF-trap 1 polynucleotide

<400> SEQUENCE: 17

```
ggccgcccct tcgtggaaat gtacagcgag atccccgaga tcatccacat gaccgagggc     60
agagagctgg tcatcccctg cagagtgacc tcccccaaca tcaccgtgac cctgaagaag    120
ttccccctgg acaccctgat ccccgacggc aagcggatca tctgggacag ccggaagggc    180
ttcatcatca gcaacgccac ctacaaagag atcgggctgc tgacctgcga ggccaccgtg    240
aacggccacc tgtacaagac caactacctg acccaccggc agaccaacac catcatcgac    300
gtggtgctga gccccagcca cggcatcgag ctgtccgtgg gcgagaagct ggtgctgaac    360
tgcaccgccc ggaccgagct gaacgtgggc atcgacttca ctgggagta ccccagcagc    420 aagcaccagc acaagaagct ggtcaaccgg gacctgaaaa cccagagcgg cagcgagatg    480
aagaagtttc tgagcaccct gacaatcgac ggcgtgacca aagcgacca gggcctgtac    540 acatcgccg ccagcagcgg cctgatgacc aagaaaaaca gcaccttcgt gcgggtgcac    600
gagaagggac ccggc                                                    615
```

<210> SEQ ID NO 18
<211> LENGTH: 675
<212> TYPE: PRT
<213> ORGANISM: Artificial Sequence
<220> FEATURE:
<223> OTHER INFORMATION: Description of Artificial Sequence: Synthetic
      sc4D5-VEGF-trap(Fc) 1 fusion polypeptide

<400> SEQUENCE: 18

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80
```

```
Leu Gln Met Asn Ser Leu Arg Ala Glu Asp Thr Ala Val Tyr Tyr Cys
                85                  90                  95
Ser Arg Trp Gly Gly Asp Gly Phe Tyr Ala Met Asp Tyr Trp Gly Gln
            100                 105                 110
Gly Thr Leu Val Thr Val Ser Ser Gly Gly Gly Ser Gly Gly Gly
        115                 120                 125
Gly Ser Gly Gly Gly Ser Asp Ile Gln Met Thr Gln Ser Pro Ser
130                 135                 140
Ser Leu Ser Ala Ser Val Gly Asp Arg Val Thr Ile Thr Cys Arg Ala
145                 150                 155                 160
Ser Gln Asp Val Asn Thr Ala Val Ala Trp Tyr Gln Gln Lys Pro Gly
                165                 170                 175
Lys Ala Pro Lys Leu Leu Ile Tyr Ser Ala Ser Phe Leu Tyr Ser Gly
            180                 185                 190
Val Pro Ser Arg Phe Ser Gly Ser Arg Ser Gly Thr Asp Phe Thr Leu
        195                 200                 205
Thr Ile Ser Ser Leu Gln Pro Glu Asp Phe Ala Thr Tyr Tyr Cys Gln
    210                 215                 220
Gln His Tyr Thr Thr Pro Pro Thr Phe Gly Gln Gly Thr Lys Val Glu
225                 230                 235                 240
Ile Lys Arg Gly Arg Pro Phe Val Glu Met Tyr Ser Glu Ile Pro Glu
                245                 250                 255
Ile Ile His Met Thr Glu Gly Arg Glu Leu Val Ile Pro Cys Arg Val
            260                 265                 270
Thr Ser Pro Asn Ile Thr Val Thr Leu Lys Lys Phe Pro Leu Asp Thr
        275                 280                 285
Leu Ile Pro Asp Gly Lys Arg Ile Ile Trp Asp Ser Arg Lys Gly Phe
    290                 295                 300
Ile Ile Ser Asn Ala Thr Tyr Lys Glu Ile Gly Leu Leu Thr Cys Glu
305                 310                 315                 320
Ala Thr Val Asn Gly His Leu Tyr Lys Thr Asn Tyr Leu Thr His Arg
                325                 330                 335
Gln Thr Asn Thr Ile Ile Asp Val Val Leu Ser Pro Ser His Gly Ile
            340                 345                 350
Glu Leu Ser Val Gly Glu Lys Leu Val Leu Asn Cys Thr Ala Arg Thr
        355                 360                 365
Glu Leu Asn Val Gly Ile Asp Phe Asn Trp Glu Tyr Pro Ser Ser Lys
    370                 375                 380
His Gln His Lys Lys Leu Val Asn Arg Asp Leu Lys Thr Gln Ser Gly
385                 390                 395                 400
Ser Glu Met Lys Lys Phe Leu Ser Thr Leu Thr Ile Asp Gly Val Thr
                405                 410                 415
Arg Ser Asp Gln Gly Leu Tyr Thr Cys Ala Ala Ser Ser Gly Leu Met
            420                 425                 430
Thr Lys Lys Asn Ser Thr Phe Val Arg Val His Glu Lys Gly Pro Gly
        435                 440                 445
Asp Lys Thr His Thr Cys Pro Pro Cys Pro Ala Pro Glu Leu Leu Gly
    450                 455                 460
Gly Pro Ser Val Phe Leu Phe Pro Pro Lys Pro Lys Asp Thr Leu Met
465                 470                 475                 480
Ile Ser Arg Thr Pro Glu Val Thr Cys Val Val Val Asp Val Ser His
                485                 490                 495
Glu Asp Pro Glu Val Lys Phe Asn Trp Tyr Val Asp Gly Val Glu Val
```

```
            500                 505                 510
His Asn Ala Lys Thr Lys Pro Arg Glu Glu Gln Tyr Asn Ser Thr Tyr
        515                 520                 525

Arg Val Ser Val Leu Thr Val Leu His Gln Asp Trp Leu Asn Gly
    530                 535                 540

Lys Glu Tyr Lys Cys Lys Val Ser Asn Lys Ala Leu Pro Ala Pro Ile
545                 550                 555                 560

Glu Lys Thr Ile Ser Lys Ala Lys Gly Gln Pro Arg Glu Pro Gln Val
                565                 570                 575

Tyr Thr Leu Pro Pro Ser Arg Asp Glu Leu Thr Lys Asn Gln Val Ser
            580                 585                 590

Leu Thr Cys Leu Val Lys Gly Phe Tyr Pro Ser Asp Ile Ala Val Glu
        595                 600                 605

Trp Glu Ser Asn Gly Gln Pro Glu Asn Asn Tyr Lys Thr Thr Pro Pro
    610                 615                 620

Val Leu Asp Ser Asp Gly Ser Phe Phe Leu Tyr Ser Lys Leu Thr Val
625                 630                 635                 640

Asp Lys Ser Arg Trp Gln Gln Gly Asn Val Phe Ser Cys Ser Val Met
                645                 650                 655

His Glu Ala Leu His Asn His Tyr Thr Gln Lys Ser Leu Ser Leu Ser
            660                 665                 670

Pro Gly Lys
        675

<210> SEQ ID NO 19
<211> LENGTH: 645
<212> TYPE: DNA
<213> ORGANISM: Artificial Sequence
<220> FEATURE:
<223> OTHER INFORMATION: Description of Artificial Sequence: Synthetic
      VEGF-trap 2 polynucleotide

<400> SEQUENCE: 19
ggccgctacg tgcaggacta cagaagcccc tttatcgcca gcgtgtccga ccagcacggc        60
gtggtgtaca tcaccgagaa caagaacaag accgtggtga tccccctgcct gggcagcatc      120 agcaacctga acgtgtccct gtgcgccaga taccccgaga agagattcgt gcccgacggc      180
aaccggatca gctgggacag caagaagggc ttcaccatcc ccagctacat gatcagctac      240
gccggcatgg tgttctgcga ggccaagatc aacgacgaga gctaccagag catcatgtac      300
atcgtggtgg tggtgggata ccggatcgac gtggtgctga gccccagcca cggcatcgag      360
ctgtccgtgg gcgagaagct ggtgctgaac tgcaccgccc ggaccgagct gaacgtgggc      420
atcgacttca ctggggagta ccccagcagc aagcaccagc acaagaagct ggtcaaccgg      480
gacctgaaaa cccagagcgg cagcgagatg aagaagtttc tgagcaccct gacaatcgac      540
ggcgtgacca aagcgaccag ggcctgtac acatgcgccg ccagcagcgg cctgatgacc       600
aagaaaaaca gcaccttcgt gcgggtgcac gagaagggac ccggc                     645

<210> SEQ ID NO 20
<211> LENGTH: 1344
<212> TYPE: DNA
<213> ORGANISM: Artificial Sequence
<220> FEATURE:
<223> OTHER INFORMATION: Description of Artificial Sequence: Synthetic
      sc4D5-VEGF-trap 1 fusion polynucleotide

<400> SEQUENCE: 20
```

```
gaggtgcagc tggtggaaag cggcggaggc ctggtgcagc ctggcggaag cctgagactg      60
agctgtgccg ccagcggctt caacatcaag gacacctaca tccactgggt ccgacaggcc     120
cctggcaagg gcctggaatg ggtggcccgg atctacccca ccaacggcta caccagatac     180
gccgacagcg tgaagggccg gttcaccatc agcgccgaca ccagcaagaa caccgcctac     240
ctgcagatga acagcctgcg ggccgaggac accgccgtgt actactgcag cagatgggga     300
ggcgacggct tctacgccat ggactactgg ggccagggca ccctggtcac cgtgtctagc     360
ggaggcggcg gatctggcgg cggaggaagt ggcggaggcg gaagcgacat ccagatgacc     420
cagagcccca gcagcctgag cgccagcgtg ggcgacagag tgaccatcac ctgtcgggcc     480
agccaggacg tgaacacagc cgtggcctgg tatcagcaga agcccggcaa ggccccaag      540
ctgctgatct acagcgccag cttcctgtac agcggcgtgc ccagccggtt cagcggcagc     600
agaagcggca ccgacttcac cctgaccatc tccagcctgc agcccgagga tttcgccacc     660
tactattgcc agcagcacta caccaccccc cccaccttcg gacagggcac caaggtggaa     720
atcaagcgcg gccgcccctt cgtggaaatg tacagcgaga tccccgagat catccacatg     780
accgagggca gagagctggt catcccctgc agagtgacct cccccaacat caccgtgacc     840
ctgaagaagt tccccctgga caccctgatc cccgacggca gcggatcat ctgggacagc     900
cggaagggct tcatcatcag caacgccacc tacaaagaga tcgggctgct gacctgcgag     960
gccaccgtga acggccacct gtacaagacc aactacctga cccaccggca gaccaacacc    1020
atcatcgacg tggtgctgag ccccagccac ggcatcgagc tgtccgtggg cgagaagctg    1080
gtgctgaact gcaccgcccg gaccgagctg aacgtgggca tcgacttcaa ctgggagtac    1140
cccagcagca gcaccagca agaagctg gtcaaccggg acctgaaaac ccagagcggc    1200
agcgagatga agaagtttct gagcaccctg acaatcgacg gcgtgaccag aagcgaccag    1260
ggcctgtaca catcgccgc cagcagcggc ctgatgacca gaaaaacag caccttcgtg    1320
cgggtgcacg agaagggacc cggc                                          1344
```

<210> SEQ ID NO 21
<211> LENGTH: 458
<212> TYPE: PRT
<213> ORGANISM: Artificial Sequence
<220> FEATURE:
<223> OTHER INFORMATION: Description of Artificial Sequence: Synthetic sc4D5-VEGF-trap 2 fusion polypeptide

<400> SEQUENCE: 21

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
```

```
            115                 120                 125
Gly Ser Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Asp Val Asn Thr Ala Val Ala Trp Tyr Gln Lys Pro Gly
                165                 170                 175

Lys Ala Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
210                 215                 220

Gln His Tyr Thr Thr Pro Pro Thr Phe Gly Gln Gly Thr Lys Val Glu
225                 230                 235                 240

Ile Lys Arg Gly Arg Tyr Val Gln Asp Tyr Arg Ser Pro Phe Ile Ala
                245                 250                 255

Ser Val Ser Asp Gln His Gly Val Val Tyr Ile Thr Glu Asn Lys Asn
            260                 265                 270

Lys Thr Val Val Ile Pro Cys Leu Gly Ser Ile Ser Asn Leu Asn Val
        275                 280                 285

Ser Leu Cys Ala Arg Tyr Pro Glu Lys Arg Phe Val Pro Asp Gly Asn
    290                 295                 300

Arg Ile Ser Trp Asp Ser Lys Lys Gly Phe Thr Ile Pro Ser Tyr Met
305                 310                 315                 320

Ile Ser Tyr Ala Gly Met Val Phe Cys Glu Ala Lys Ile Asn Asp Glu
                325                 330                 335

Ser Tyr Gln Ser Ile Met Tyr Ile Val Val Val Gly Tyr Arg Ile
            340                 345                 350

Asp Val Val Leu Ser Pro Ser His Gly Ile Glu Leu Ser Val Gly Glu
        355                 360                 365

Lys Leu Val Leu Asn Cys Thr Ala Arg Thr Glu Leu Asn Val Gly Ile
    370                 375                 380

Asp Phe Asn Trp Glu Tyr Pro Ser Ser Lys His Gln His Lys Lys Leu
385                 390                 395                 400

Val Asn Arg Asp Leu Lys Thr Gln Ser Gly Ser Glu Met Lys Lys Phe
                405                 410                 415

Leu Ser Thr Leu Thr Ile Asp Gly Val Thr Arg Ser Asp Gln Gly Leu
            420                 425                 430

Tyr Thr Cys Ala Ala Ser Ser Gly Leu Met Thr Lys Lys Asn Ser Thr
        435                 440                 445

Phe Val Arg Val His Glu Lys Gly Pro Gly
    450                 455

<210> SEQ ID NO 22
<211> LENGTH: 1374
<212> TYPE: DNA
<213> ORGANISM: Artificial Sequence
<220> FEATURE:
<223> OTHER INFORMATION: Description of Artificial Sequence: Synthetic
      sc4D5-VEGF-trap 2 fusion polynucleotide

<400> SEQUENCE: 22
gaggtgcagc tggtggaaag cggcggaggc ctggtgcagc ctggcggaag cctgagactg      60
agctgtgccg ccagcggctt caacatcaag gacaccctac tccactgggt ccgacaggcc     120
```

-continued

```
cctggcaagg gcctggaatg ggtggcccgg atctacccca ccaacggcta caccagatac      180
gccgacagcg tgaagggccg gttcaccatc agcgccgaca ccagcaagaa caccgcctac      240
ctgcagatga acagcctgcg ggccgaggac accgccgtgt actactgcag cagatgggga      300
ggcgacggct tctacgccat ggactactgg ggccagggca ccctggtcac cgtgtctagc      360
ggaggcggcg gatctggcgg cggaggaagt ggcggaggcg gaagcgacat ccagatgacc      420
cagagcccca gcagcctgag cgccagcgtg ggcgacagag tgaccatcac ctgtcgggcc      480
agccaggacg tgaacacagc cgtggcctgg tatcagcaga agcccggcaa ggccccccaag      540 ctgctgatct cagcgccag cttcctgtac agcggcgtgc ccagccggtt cagcggcagc      600
agaagcggca ccgacttcac cctgaccatc tccagcctgc agcccgagga tttcgccacc      660
tactattgcc agcagcacta caccacccc cccaccttcg acagggcac caaggtggaa      720 atcaagcgcg gcgctacgt gcaggactac agaagcccct ttatcgccag cgtgtccgac      780
cagcacggcg tggtgtacat caccgagaac aagaacaaga ccgtggtgat ccccctgcctg      840 ggcagcatca gcaacctgaa cgtgtccctg tgcgccagat accccgagaa gagattcgtg      900
cccgacggca accggatcag ctgggacagc aagaagggct tcaccatccc cagctacatg      960
atcagctacg ccggcatggt gttctgcgag gccaagatca acgacgagag ctaccagagc     1020
atcatgtaca cgtggtggt ggtgggatac cggatcgacg tggtgctgag ccccagccac     1080
ggcatcgagc tgtccgtggg cgagaagctg gtgctgaact gcaccgcccg gaccgagctg     1140
aacgtgggca tcgacttcaa ctgggagtac cccagcagca agcaccagca caagaagctg     1200
gtcaaccggg acctgaaaac ccagagcggc agcgagatga agaagtttct gagcaccctg     1260
acaatcgacg gcgtgaccag aagcgaccag ggcctgtaca catgcgccgc cagcagcggc     1320
ctgatgacca agaaaaacag caccttcgtg cgggtgcacg agaagggacc cggc          1374
```

<210> SEQ ID NO 23
<211> LENGTH: 685
<212> TYPE: PRT
<213> ORGANISM: Artificial Sequence
<220> FEATURE:
<223> OTHER INFORMATION: Description of Artificial Sequence: Synthetic sc4D5-VEGF-trap(Fc) 2 fusion polypeptide

<400> SEQUENCE: 23

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
```

```
            130             135             140
Ser Leu Ser Ala Ser Val Gly Asp Arg Val Thr Ile Thr Cys Arg Ala
145             150             155             160

Ser Gln Asp Val Asn Thr Ala Val Ala Trp Tyr Gln Gln Lys Pro Gly
            165             170             175

Lys Ala Pro Lys Leu Leu Ile Tyr Ser Ala Ser Phe Leu Tyr Ser Gly
            180             185             190

Val Pro Ser Arg Phe Ser Gly Ser Arg Ser Gly Thr Asp Phe Thr Leu
            195             200             205

Thr Ile Ser Ser Leu Gln Pro Glu Asp Phe Ala Thr Tyr Tyr Cys Gln
            210             215             220

Gln His Tyr Thr Thr Pro Pro Thr Phe Gly Gln Gly Thr Lys Val Glu
225             230             235             240

Ile Lys Arg Gly Arg Tyr Val Gln Asp Tyr Arg Ser Pro Phe Ile Ala
            245             250             255

Ser Val Ser Asp Gln His Gly Val Val Tyr Ile Thr Glu Asn Lys Asn
            260             265             270

Lys Thr Val Val Ile Pro Cys Leu Gly Ser Ile Ser Asn Leu Asn Val
            275             280             285

Ser Leu Cys Ala Arg Tyr Pro Glu Lys Arg Phe Val Pro Asp Gly Asn
290             295             300

Arg Ile Ser Trp Asp Ser Lys Lys Gly Phe Thr Ile Pro Ser Tyr Met
305             310             315             320

Ile Ser Tyr Ala Gly Met Val Phe Cys Glu Ala Lys Ile Asn Asp Glu
            325             330             335

Ser Tyr Gln Ser Ile Met Tyr Ile Val Val Val Gly Tyr Arg Ile
            340             345             350

Asp Val Val Leu Ser Pro Ser His Gly Ile Glu Leu Ser Val Gly Glu
            355             360             365

Lys Leu Val Leu Asn Cys Thr Ala Arg Thr Glu Leu Asn Val Gly Ile
370             375             380

Asp Phe Asn Trp Glu Tyr Pro Ser Ser Lys His Gln His Lys Lys Leu
385             390             395             400

Val Asn Arg Asp Leu Lys Thr Gln Ser Gly Ser Glu Met Lys Lys Phe
            405             410             415

Leu Ser Thr Leu Thr Ile Asp Gly Val Thr Arg Ser Asp Gln Gly Leu
            420             425             430

Tyr Thr Cys Ala Ala Ser Ser Gly Leu Met Thr Lys Lys Asn Ser Thr
            435             440             445

Phe Val Arg Val His Glu Lys Gly Pro Gly Asp Lys Thr His Thr Cys
            450             455             460

Pro Pro Cys Pro Ala Pro Glu Leu Leu Gly Gly Pro Ser Val Phe Leu
465             470             475             480

Phe Pro Pro Lys Pro Lys Asp Thr Leu Met Ile Ser Arg Thr Pro Glu
            485             490             495

Val Thr Cys Val Val Val Asp Val Ser His Glu Asp Pro Glu Val Lys
            500             505             510

Phe Asn Trp Tyr Val Asp Gly Val Glu Val His Asn Ala Lys Thr Lys
            515             520             525

Pro Arg Glu Glu Gln Tyr Asn Ser Thr Tyr Arg Val Val Ser Val Leu
            530             535             540

Thr Val Leu His Gln Asp Trp Leu Asn Gly Lys Glu Tyr Lys Cys Lys
545             550             555             560
```

```
Val Ser Asn Lys Ala Leu Pro Ala Pro Ile Glu Lys Thr Ile Ser Lys
            565                 570                 575
Ala Lys Gly Gln Pro Arg Glu Pro Gln Val Tyr Thr Leu Pro Pro Ser
        580                 585                 590
Arg Asp Glu Leu Thr Lys Asn Gln Val Ser Leu Thr Cys Leu Val Lys
    595                 600                 605
Gly Phe Tyr Pro Ser Asp Ile Ala Val Glu Trp Glu Ser Asn Gly Gln
610                 615                 620
Pro Glu Asn Asn Tyr Lys Thr Thr Pro Pro Val Leu Asp Ser Asp Gly
625                 630                 635                 640
Ser Phe Phe Leu Tyr Ser Lys Leu Thr Val Asp Lys Ser Arg Trp Gln
            645                 650                 655
Gln Gly Asn Val Phe Ser Cys Ser Val Met His Glu Ala Leu His Asn
        660                 665                 670
His Tyr Thr Gln Lys Ser Leu Ser Leu Ser Pro Gly Lys
    675                 680                 685

<210> SEQ ID NO 24
<211> LENGTH: 2058
<212> TYPE: DNA
<213> ORGANISM: Artificial Sequence
<220> FEATURE:
<223> OTHER INFORMATION: Description of Artificial Sequence: Synthetic
      sc4D5-VEGF-trap(Fc) 2 fusion polynucleotide

<400> SEQUENCE: 24
gaggtgcagc tggtggaaag cggcggaggc ctggtgcagc ctggcggaag cctgagactg      60
agctgtgccg ccagcggctt caacatcaag gacacctaca tccactgggt ccgacaggcc     120
cctggcaagg gcctggaatg ggtggcccgg atctacccca ccaacggcta caccagatac     180
gccgacagcg tgaagggccg gttcaccatc agcgccgaca ccagcaagaa caccgcctac     240
ctgcagatga acagcctgcg ggccgaggac accgccgtgt actactgcag cagatgggga     300
ggcgacggct tctacgccat ggactactgg ggccagggca cctggtcac cgtgtctagc     360
ggaggcggcg gatctggcgg cggaggaagt ggcggaggcg gaagcgacat ccagatgacc     420
cagagcccca gcagcctgag cgccagcgtg ggcgacagag tgaccatcac ctgtcgggcc     480
agccaggacg tgaacacagc cgtggcctgg tatcagcaga agcccggcaa ggcccccaag     540
ctgctgatct acagcgccag cttcctgtac agcggcgtgc ccagccggtt cagcggcagc     600
agaagcggca ccgacttcac cctgaccatc tccagcctgc agcccgagga tttcgccacc     660
tactattgcc agcagcacta caccaccccc ccaccttcg acagggcac aaggtggaa      720
atcaagcgcg ccgctacgt gcaggactac agaagcccct ttatcgccag cgtgtccgac     780
cagcacggcg tggtgtacat caccgagaac aagaacaaga ccgtggtgat ccctgcctg     840
ggcagcatca gcaacctgaa cgtgtccctg tgcgccagat accccgagaa gagattcgtg     900
cccgacggca accggatcag ctgggacagc aagaagggct tcaccatccc cagctacatg     960
atcagctacg ccggcatggt gttctgcgag gccaagatca cgacgagag ctaccagagc    1020
atcatgtaca tcgtggtggt ggtgggatac cggatcgacg tggtgctgag ccccagccac    1080
ggcatcgagc tgtccgtggg cgagaagctg gtgctgaact gcaccgcccg gaccgagctg    1140
aacgtgggca tcgacttcaa ctgggagtac cccagcagca gcaccagca caagaagctg    1200
gtcaaccggg acctgaaaac ccagagcggc agcgagatga agaagtttct gagcaccctg    1260
acaatcgacg gcgtgaccag aagcgaccag ggcctgtaca catgcgccgc cagcagcggc    1320
```

```
ctgatgacca agaaaaacag caccttcgtg cgggtgcacg agaagggacc cggcgacaag    1380
acccacacct gtccccttg ccctgcccct gagctgctgg gaggcccttc cgtgtttctg    1440 ttcccccaa agcccaagga taccctgatg atcagccgga cccccgaagt gacctgcgtg    1500
gtggtggacg tgtcccacga ggaccctgaa gtgaagttca attggtacgt ggacggcgtg    1560
gaagtgcaca acgccaagac caagcccaga gaggaacagt acaacagcac ctaccgggtg    1620
gtgtccgtgc tgaccgtgct gcaccaggac tggctgaacg gcaaagagta caagtgcaag    1680
gtctccaaca aggccctgcc tgcccccatc gagaaaacca tcagcaaggc caagggccag    1740
ccccgcgagc ctcaggtgta cactgccc cccagccggg acgagctgac caagaaccag    1800
gtgtccctga cctgcctggt caagggcttc taccccagcg atatcgccgt ggaatgggag    1860
agcaacggcc agcccgagaa caactacaag accacccctc ccgtgctgga cagcgacggc    1920
tcattcttcc tgtactccaa gctgaccgtg gacaagagcc ggtggcagca gggcaacgtg    1980
ttcagctgca gcgtgatgca cgaggccctg cacaaccact acacccagaa gtccctgagc    2040
ctgagccccg gcaaatga                                                  2058

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 25

His His His His His His
1               5
```

FUSION PROTEIN FOR SUPPRESSING CANCER CELL GROWTH AND SUPPRESSING VASCULOGENESIS, AND ANTICANCER COMPOSITION COMPRISING SAME

CROSS REFERENCE TO RELATED APPLICATIONS

This is a National Stage of International Application No. PCT/KR2012/004531 filed Jun. 8, 2012, claiming priority based on Korean Patent Application No. 10-2011-0056089 filed Jun. 10, 2011 and Korean Patent Application No. 10-2012-0061054 filed Jun. 7, 2012, the contents of all of which are incorporated herein by reference in their entirety.

TECHNICAL FIELD

The present invention relates to a fusion protein for inhibiting cancer cell proliferation and inhibiting angiogenesis and an anti-cancer composition containing the same, and more specifically, to a fusion protein in which a cancer-specific antibody is bound to an angiogenesis inhibitor and an anti-cancer composition containing the same.

BACKGROUND ART

In order for cancer cells to proliferate and grow, new blood vessels are required to supply oxygen and nutrients. Various factors are involved in angiogenesis; however, among them, a vascular endothelial growth factor (VEGF) serves as the most important regulator (see Ferrara and Davis-Smyth (1997) Endocrine Rev. 18: 4-25; Ferrara (1999) J. Mol. Med. 77:527-543).

VEGF is a dimer configuring sub-units and having a molecular weight of about 46 KDa, the sub-unit having a molecular weight of about 23 KDa and regulates vasculogenesis at an embryogenesis as well as angiogenesis in an adult organism. Five kinds of VEGFs (VEGF-A, VEGF-B, VEGF-C, VEGF-D and PLGF) have been found so far in mammals. VEGFs is bound to co-receptors such as three receptor tyrosine kinases (RTKs) known as VEGF receptors (VEGFRs) -1, -2 and -3, heparin sulphate proteoglycans (HSPGs), and neuropilin (NRPB) in an overlapped scheme. The VEGF receptor causes cell migration, survival, and proliferation, like many growth factor receptors, and has functions of delivering a signal capable of forming a three-dimensional blood vessel or controlling a blood vessel permeability, wherein the functions are not found in the other RTKs.

It has been found through a target gene inactivation research in mice that VEGF is a factor required for an early stage of angiogenesis, wherein a VEGF molecule is upregulated in tumor cells and a receptor thereof is upregulated in tumor infiltrated vascular endothelial cells; however, in normal cells that are not involved in angiogenesis, expression of VEGF and the receptor thereof are maintained at low level (Brown et al., Cancer Res. 53: 4727-4735 (1993); Mattern et al., Brit. J. Cancer. 73: 931-934 (1996)). Therefore, VEGF which promotes formation of new blood vessels has drawn attention as a target for treating cancer.

Therefore, recently, a novel anti-cancer treatment for blocking production of new blood vessels has been developed, and an anti-VEGF receptor antibody, a soluble receptor structure, an antisense, an RNA aptamer that binds to VEGF, low molecular VEGF receptor tyrosine kinase (RTK) inhibitor, and the like, has been suggested in order to inhibit VEGF signaling (Siemeister et al., Cancer Metastasis Rev. 17: 241-248 (1998)). Subsequently, it has been found in nude mice that an anti-VEGF neutralizing antibody inhibits growth of various human tumor cell lines (Warren et al., J. Clin. Invest. 95: 1789-1797 (1995); Borgstrom et al., Cancer Res. 56: 4032-4039 (1996); and Melnyk et al., Cancer Res. 56: 921-924 (1996)).

Among patent documents related to the VEGF inhibitor, U.S. Pat. No. 6,011,003 discloses an altered, soluble form of FMS-like tyrosine kinase receptor (FLT) polypeptide including immunoglobulin domains exerting an inhibitory effect on VEGF, and WO 98/13071 discloses gene therapy for inhibiting primary tumor growth and metastasis by gene transfer of a nucleotide sequence encoding soluble receptor protein which binds to VEGF. In addition, WO 97/13787 discloses a low-molecular VEGF inhibitor usable in treatment of diseases accompanied by neovascularization, and WO 00/75319 discloses modified polypeptides including sequences of modified Flt 1 and Flt 4 which are VEGF receptor.

An angiogenesis inhibitor according to the related art inhibits an angiogenesis, which is required for cancer growth; however, since the angiogenesis inhibitor does not have a targeting function against tumor cells, a cancer cell-specific anti-cancer effect is not capable of being exerted, and side effects may occur on normal blood vessels. Subsequently, in the case of Bevacizumab (Avastin™) commercially available as a humanized antibody to VEGF, it was announced from phase III clinical trials by Genentech, Inc., that intestinal bleeding, hemoptysis, hemorrhage, epistaxis, coughing up blood as side effects were observed, and headaches, high blood pressure, nasal swelling, albuminuria, dry skin, excessive tears, back pain, skin edema, and the like, were also observed. It is considered that the above-described side effects are shown since the angiogenesis inhibitor according to the related art does not have a targeting function against tumor cells.

Therefore, it is necessary to develop an anti-cancer agent capable of effectively treating cancer by effectively delivering an angiogenesis inhibitor to cancer through selective targeting of cancer cells to reduce side effects and to effectively inhibit angiogenesis required for cancer growth, and by directly inhibiting the cancer cells.

Technical Problem

An object of the present invention is to provide a fusion protein capable of providing an anti-cancer agent effectively treating cancer by linking a cancer-specific antibody and an angiogenesis inhibitor to reduce side effects and to effectively inhibit angiogenesis required for cancer growth, and by directly inhibiting the cancer cells.

Another object of the present invention is to provide a nucleotide encoding the fusion protein, a recombinant vector including the same, and a host cell transformed with the recombinant vector.

Another object of the present invention is to provide a method for producing a fusion protein including incubating a host cell transformed with a recombinant vector and bonding a cancer-specific antibody to an angiogenesis inhibitor.

Another object of the present invention is to provide an anti-cancer pharmaceutical composition including the fusion protein and an anti-cancer treatment using the same.

Technical Solution

In one general aspect, a fusion protein in which a cancer-specific antibody is bound to an angiogenesis inhibitor may be provided.

A term: "angiogenesis" in the present invention means a phenomenon in which vascular endothelial cells are proliferated and reconstituted to form a new blood vessel from the existing vessel network. Angiogenesis factors promoting blood vessel generation, endothelial cell growth, blood vessel stability, and blood vessel formation are involved in the angiogenesis. The angiogenesis factors include members of vascular endothelial growth factor (VEGF) family, placental growth factor (PlGF) family, platelet-derived growth factor (PDGF) family, fibroblast growth factor (FGF) family, TIE ligand (angiopoietin), ephrin, Del-1, follistatin, granulocyte colony-stimulating factor (G-CSF), hepatocyte growth factor (HGF)/scatter factor (SF), interleukin-8 (IL-8), leptin, midkine, placental growth factor, platelet-derived endothelial cell growth factor (PD-ECGF), in particular, PDGF-BB or PDGFR-beta, pleiotrophin (PTN), progranulin, proliferin, transforming growth factor-alpha (TGF-alpha), transforming growth factor-beta (TGF-beta), tumor necrosis factor-alpha (TNF-alpha), vascular permeation factor (VPF), and the like, but is not particularly limited thereto.

A term: "angiogenesis inhibitor" in the present invention means a low-molecular weight material, a polynucleotide, polypeptide, isolated protein, recombinant protein, antibody, or a conjugate or a fusion protein thereof, which directly or indirectly inhibit blood vessel generation, blood vessel formation, or undesirable blood vessel permeability. In addition, the angiogenesis inhibitor includes a material which binds to the angiogenesis factor or a receptor thereof to block the angiogenesis from being activated. For example, the angiogenesis inhibitor includes an antibody to an angiogenesis agent or other antagonists, for example, an antibody to VEGF-A or VEGF-A receptor (for example, KDR receptor or Flt-1 Ceceptor), VEGF-trap, and an antibody to angiopoietin 2.

Preferably, the VEGF-trap as the angiogenesis inhibitor is used in the fusion protein according to the present invention. The VEGF-trap in the present invention means a multimeric protein capable of binding to the VEGF, and means a material useful for treating VEGF-related conditions and diseases that are improved, alleviated, or inhibited by removal, inhibition, or reduction of VEGF. Preferably, the VEGF-trap according to the present invention has amino acid sequence of SEQ. ID. NO: 13 or SEQ. ID. NO: 14, and a fusion protein including polypeptide consisting of fragments of SEQ. ID. NO: 13 or SEQ. ID. NO: is included in the claimed range of the present invention as long as properties of the VEGF-trap binding to the VEGF are maintained.

In addition, in the VEGF-trap according to the present invention, a human immunoglobulin G1 (IgG1) Fc region of SEQ. ID. NO: 15 is further bound (VEGF-trap (Fc)) to C-terminal of the VEGF-trap, wherein the VEGF-trap (Fc) has amino acid sequence of SEQ. ID. NO: 1 or SEQ. ID. NO: 12, and a fusion protein including polypeptide consisting of fragments of SEQ. ID. NO: 1 or SEQ. ID. NO: 12 is included in the claimed range of the present invention as long as properties of the VEGF-trap capable of binding to the VEGF are maintained.

A term: "cancer-specific antibody" in the present invention means an antibody capable of inhibiting a cancer cell proliferation by specifically binding to a cancer-related antigen specifically expressed or excessively expressed in a cancer cell surface or a cancer tissue. As a cancer-specific antibody, a fragment of antibody molecule may be used as well as a complete form of antibody consisting of two light chains having the entire length and two heavy chains having the entire length. A fragment of the antibody molecule means a fragment possessing an antigen binding function and includes a single-chain Fv(scFv), Fab, F(ab'), F(ab')$_2$, a single domain, and the like.

A preferable cancer-specific antibody included in the fusion protein according to the present invention is not limited as long as an antibody specifically binds to a specific antigen on a cancer cell surface, and examples thereof include an anti-HER2 monoclonal antibody, in particular, trastuzumab (Herceptin™), among them, scFv of trastuzumab is preferred. It is preferred that scFv of trastuzumab consists of a heavy chain variable region having an amino acid sequence described in SEQ. ID. NO: 2 and a light chain variable region having an amino acid sequence described in SEQ. ID. NO: 3; however, as long as scFv of trastuzumab maintains a binding capacity to HER2 of trastuzumab, a fragment thereof or amino acid mutation are included in the claimed scope of the present invention. In addition, scFv of trastuzumab may be used in a form in which a heavy chain variable region having an amino acid sequence described in SEQ. ID. No: 2 and a light chain variable region having an amino acid sequence described in SEQ. ID. NO: 3 are linked by a linker, and it is preferred that a linker having sequences described in SEQ. ID. NO: 4 is used. In particular, scFv of trastuzumab having an amino acid sequence described in SEQ. ID. NO: 5 (hereinafter, which is referred to as "sc4D5") is a preferable cancer-specific antibody of the present invention.

A term: "HER2" in the present invention means an epidermal growth factor receptor (EGFR) 2 which is one of the important signaling cascades related to proliferation and survival of breast cancer cell. It is known that receptor tyrosine kinases of EGFR family consist of four elements, that is, erbB1, erbB2/HER2 and erbB3, erbB4, and are involved in controlling adhesion, migration, and differentiation of a cell, in addition to cell proliferation and cell survival. ErbB2/HER2 among four erbB families is known to be the strongest oncoprotein in breast cancer even though ErbB2/HER2 does not have a ligand bound thereto. HER2 is involved in growth and development of normal mammary gland tissue at a normal level; however, in the case in which HER2 is abnormally overexpressed, normal cells are not controlled and malignant cancer cells are formed in a mammary gland tissue. That is, in the case in which HER2 is oligomerized with the other EGFR families and activated to phosphorylate many downstream molecules and sequentially activate various signaling cascades, wherein a SOS-Ras-Raf-MEK-MAPK pathway involved in cell proliferation and a PI-3K/Akt pathway inhibiting cell apoptosis are representative mechanism involved in cancer proliferation.

As results of preclinical and clinical testings, HER2 overexpression is an important phenomenon expressed from an initial stage of cancer development and plays an important role for cancer growth and progression. HER2 overexpression is detected in about 20 to 30% of invasive breast cancer and is known to be associated with a poor prognosis of a patient suffering from breast cancer.

A term: trastuzumab in the present invention means a recombinant humanized monoclonal antibody targeting extracellular domains of HER2. In the case in which trastuzumab is bound to the extracellular domains of HER2 overexpressed in a cancer cell, activated signaling cascades is inhibited. Therefore, a fusion protein obtained by linking an anti-HER2 monoclonal antibody as a cancer-specific antibody according to the present invention, preferably, trastuzumab, to the angiogenesis inhibitor may inhibit cancer cell proliferation and may effectively inhibit angiogenesis, leading to treat cancer, due to the presence of trastuzumab and angiogenesis inhibitor.

Since the cancer-specific antibody is linked to the angiogenesis inhibitor in the fusion protein according to the present invention and a selective targeting of cancer cells is possible in delivering the angiogenesis inhibitor, desired effects may be achieved even at a low dose. In addition, as an antibody remarkably inhibiting cancer cell proliferation is used, the angiogenesis may be effectively inhibited and therefore cancer growth may be effectively inhibited.

A term: "fusion protein" in the present invention generally means a protein having a form in which heterologous proteins are linked to each other, and a protein having a form in which a cancer-specific antibody is linked to an angiogenesis inhibitor. Since the fusion protein according to the present invention includes the cancer-specific antibody and the angiogenesis inhibitor linked to each other, and a selective targeting of cancer cells is possible in delivering the angiogenesis inhibitor, the angiogenesis may be effectively inhibited and cancer growth may be effectively inhibited.

In the fusion protein in the present invention, the cancer-specific antibody may be linked to the N-terminus or C-terminus of the angiogenesis inhibitor. Gene sequences encoding the fusion protein may be directly linked thereto or linked through a linker. The fusion protein according to the present invention in which the N-terminus of VEGF-trap having amino acid sequence described in SEQ. ID. NO: 13 is linked to the C-terminus of sc4D5 having amino acid sequence described in SEQ. ID. NO: 5, has amino acid sequence described in SEQ. ID. NO: 6.

In addition, the fusion protein according to the present invention in which the N-terminus of VEGF-trap having amino acid sequence described in SEQ. ID. NO: 14 is linked to the C-terminus of sc4D5 having amino acid sequence described in SEQ. ID. NO: 5 has amino acid sequence described in SEQ. ID. NO: 21.

In particular, it is preferred that the fusion protein according to the present invention in which the N-terminus of VEGF-trap having an amino acid sequence described in SEQ. ID. NO: 1 is linked to the C-terminus of sc4D5 having amino acid sequence described in SEQ. ID. NO: 5 and is linked to the N-terminus of human Fc having amino acid sequence described in SEQ. ID. NO: 15 has amino acid sequence described in SEQ. ID. NO: 18.

In addition, it is preferred that the fusion protein according to the present invention in which the N-terminus of VEGF-trap having an amino acid sequence described in SEQ. ID. NO: 12 is linked to the C-terminus of sc4D5 having amino acid sequence described in SEQ. ID. NO: 5 and is linked to the N-terminus of human Fc having amino acid sequence described in SEQ. ID. NO: 15 has amino acid sequence described in SEQ. ID. NO: 23.

The fusion protein is preferred to be obtained by expression and purification using a recombinant DNA method. More specifically, genes in which the gene encoding the cancer-specific antibody is linked to the gene encoding the angiogenesis inhibitor may be expressed in a cell expression system.

In addition, the present invention provides polynucleotide sequences encoding the fusion protein and a recombinant vector including the same.

The polynucleotide sequences encoding the fusion protein may easily deduced from an amino acid sequence described in SEQ. ID. NOs: 6, 18, 21, and 23 by a person skilled in the art. In particular, polynucleotide sequences according to SEQ. ID. NO: 10 and 24 are preferred. In addition, polynucleotide sequences in which polynucleotide sequence according to SEQ. ID. NO: 11 are positioned at the 5'-end of polynucleotide sequence according to SEQ. ID. NO: 10 or 24 so that the polynucleotide encoding leader sequence according to SEQ. ID. NO: 7 is positioned at the N-terminus of the fusion protein produced according to the present invention.

A term: "recombinant vector" in the present invention is an expression vector capable of expressing a target protein in an appropriate host cell, and indicates a gene construct including essential regulation elements operably linked to each other so as to express gent inserts.

A term: "operably linked" in the present invention means that nucleic acid expression regulatory sequence is functionally linked to a polynucleotide sequence encoding desired protein so as to perform general functions. An operable link with the recombinant vector may be conducted by using gene recombinant technologies well known in the art, and site-specific DNA cleavage and linkage may be easily conducted by using enzymes generally known in the art.

Expression vectors appropriate for the present invention may include signal sequences for membrane-targeting or secretion in addition to expression regulatory elements such as a promoter, an initiation codon, a termination codon, a polyadenylation signal, and an enhancer. The initiation codon and the termination codon are generally considered as portions of nucleotide sequences encoding a target protein, and at the time of administering the gene construct, the corresponding subject is required to show function and should be in frame with coding sequences. A general promoter may be constitutive or inducible. Promoters of prokaryotic cells include lac, tac, T3 and T7 promoters, but the present invention is not limited thereto. Promoters of eukaryotic cells include a monkey virus 40 (SV40) promoter, a mouse mammary tumor virus (MMTV) promoter, a human immunodeficiency virus (HIV), for example, a HIV long terminal repeats (LTR) promoter, a moloney virus, cytomegalovirus (CMV), an Epstein Barr virus (EBV), a rous sarcoma virus (RSV) promoter, and also have a β-actin promoter, a human hemoglobin-, human tissue creatine-, human metallothionein-derived promoter, but the present invention is not limited thereto.

The expression vector may include a selective marker for selecting a host cell containing vector. A selective marker is a vector for selecting a transformed cell, and may include markers providing selectable phenotype such as drug resistance, auxotrophy, resistance to a cytotoxic agent or expression of a surface protein. Since cells only expressing the selective marker survive in an environment treated with the selective agent, the transformed cells are selectable. In addition, in the case in which the vector is a replicative expression vector, vector may include an origin of replication that is a specific nucleotide sequence initiating replication.

As a recombinant expression vector for inserting foreign genes, various vectors such as plasmid, virus, cosmid vector, and the like, may be used. The recombinant vector in the present invention is not particularly limited in view of a kind as long as the recombinant vector expresses desired genes in each host cell including prokaryotic cells and eukaryotic cells and produces desired proteins; however, a vector capable of mass-producing foreign protein maintaining strong expression with a promoter showing strong activation and having a similar form to a nature state is preferred.

In order to express the fusion protein according to the present invention, various expression host/vector combinations may be used. Examples of an expression vector appropriate for a eukaryotic host include expression regulatory sequences derived from monkey virus 40 (SV40), bovine papilloma virus, adenovirus, adeno-associated virus, cytomegalovirus and retro virus, but the present invention is not limited thereto. The expression vector capable of being used in a bacterial host cell includes bacterial plasmids obtained from *Escherichia coli*, such as pET, pRSET, pBluescript, pGEX2T, pUC vector, col E1, pCR1, pBR322, pMB9, and derivatives thereof, plasmid having a large range of host cells, such as RP4, Δgt10 and Δgt11, phage DNA including significantly various phage lambdas derivatives, such as NM989, and the other DNA phages such as M13 and filamentous single strand DNA phage. An expression vector useful for a yeast cell is 2 μm plasmid and derivatives thereof. A vector useful for an insect cell is pVL941.

According to another embodiment of the present invention, the present invention provides a host cell transformed by the recombinant vector. The recombinant vector is inserted into the host cell to form a transformant. Host cells appropriate for the vector may be prokaryotic cells such as *Escherichia coli, Bacillus subtilis, Streptomyces* sp., *Pseudomonas* sp., *Proteus mirabilis* or *Staphylococcus* sp. Host cells may also be eukaryotic cells including fungi such as *Aspergillus* sp., yeast such as *Pichia pastoris, Saccharomyces cerevisiae, Schizosaccharomyces* sp., and *Neurospora crassa*, other lower eukaryotic cells, and higher eukaryotic cells such as an insect cell, and the like. In addition, host cells may be derived from plants and mammals. Preferably, monkey kidney cell-7 (COS7), a NS0 cell, SP2/0 cell, Chinese hamster ovary (CHO) cell, W138, baby hamster kidney (BHK) cell, MDCK, myeloma cell line, HuT 78 cell, HEK293 cell, and the like, are available; however, the present invention is not limited thereto. In particular, CHO cell is preferred.

A term "transformation" into a host cell in the present invention may be performed by including any method in which nucleic acids are introduced into an organism, a cell, a tissue, or an organ, and selecting appropriate standard technology depending on the host cell as known in the art. The method for transformation includes electroporation, protoplast fusion, calcium phosphate (CaPO4) precipitation, calcium chloride (CaCl2) deposition, stirring with silicon carbide fibers, bacterium-mediated transformation, PEG, dextran sulfate, lipofectamine and dryness/inhibition-mediated transformation; however, the present invention is not limited thereto.

According to another embodiment of the present invention, the present invention provides a method for producing the fusion protein according to the present invention, the method includes incubating host cells transformed into the recombinant vector.

The method for producing the fusion protein may include: producing a recombinant vector inserting nucleotide sequences encoding the fusion protein of the present invention into a vector; transforming the recombinant vector into a host cell and incubating the transformant; and isolating and purifying the fusion protein from an incubation solution of the transformant.

More specifically, the fusion protein may be mass-produced by incubating the transformant having expressed recombinant vector in a nutrient medium, wherein medium and incubation condition may be appropriately selected depending on a host cell. Conditions such as temperature, pH of medium, incubation time, and the like, may be appropriately controlled so as to be appropriate for growth and development of cells and mass-production of protein at the time of incubation.

Recombinantly-produced peptide or protein may be recovered from medium or cell lysate. In the case of membrane-coupled type, the membrane may be isolated by using an appropriate surfactant solution (for example: tritone-X 100) or enzymatic cleavage. Cells used in expressing the fusion protein may be destroyed by various physical or chemical means such as freeze-thaw purification, sonic treatment, mechanical damage and cell decomposing agent, and may be isolated and purified by general biochemical isolation technology (Sambrook et al., Molecular Cloning: A laboratory Manual, 2nd Ed., Cold Spring Harbor Laboratory Press (1989); Deuscher, M., Guide to Protein Purification Methods Enzymology, Vol. 182. Academic Press Inc., San Diego, Calif. (1990)). Electrophoresis, centrifugation, gel filtration, precipitation, dialysis, chromatography (ion exchange chromatography, affinity chromatography, immunosorbent chromatography, size exclusion chromatography, and the like), isoelectric focusing, and various modified and composite methods thereof may be used; however, the present invention is not limited thereto.

According to another embodiment of the present invention, the present invention provides a composition for inhibiting angiogenesis or treating cancer, the composition including the fusion protein. A term "anti-cancer" in the present invention includes "prevention" and "treatment"; wherein "prevention" means all behaviors in which cancer is inhibited or delayed by administration of the composition containing the antibodies of the present invention, and "treatment" means all behaviors in which symptoms of cancer are improved or changed in an advantageous way by administration of the composition containing the antibodies of the present invention.

Cancers or tumors capable of being treated by the composition of the present invention is not particularly limited, but includes solid cancer and blood cancer. Preferably, examples of cancer include gastric cancer, breast cancer, lung cancer, ovarian cancer, liver cancer, bronchial cancer, nasopharyngeal cancer, laryngeal cancer, pancreatic cancer, bladder cancer, colorectal cancer, colon cancer, pancreas cancer, cervical cancer, brain cancer, prostate cancer, bone cancer, skin cancer, thyroid cancer, parathyroid cancer, kidney cancer, esophageal cancer, biliary tract cancer, testis cancer, rectal cancer, head and neck cancer, cervical vertebrae cancer, ureter cancer, osteosarcoma, neurocytoma, melanoma, fibrosarcoma, rhabdomyosarcoma, astrocytoma, neuroblastoma, and neuroglioma. More preferably, all cancers in which HER2 is expressed are included. The composition of the present invention is capable of treating all cancers having expressed HER2 genes; more preferably, breast cancer, gastric cancer, and the like, may be treated.

The anti-cancer composition of the present invention may additionally include a pharmaceutically acceptable carrier. In the case of oral administration, binders, lubricants, disintegrants, excipients, solubilizers, dispersants, stabilizers, suspending agents, pigments, flavoring, and the like, may be used, in the case of injections, buffers, preservatives, soothing agents, solubilizers, isotonic agents, stabilizers, and the like, may be mixed to be used, and in the case of topical administration, base agents, excipients, lubricants, preservatives, and the like, may used. The pharmaceutical composition in the present invention may be mixed with the above-described pharmaceutically acceptable carrier to have various formulations. For example, in the case of oral administration, tablets, troches, capsules, elixir, suspension, syrup, wafer, and the like, may be prepared, and in the case of injections, a unit dosage ample may be administered or may be administered at several divided times. In addition, the anti-cancer composition typically includes a surfactant capable of easily passing through membranes. Examples of the surfactant include materials derived from steroids, cationic lipids such as N-[1-(2,3-dioleoyl)propyl-N,N,N-trimethylammoniumchloride (DOTMA), various compounds such as cholesterol hemisuccinate, phosphatidyl glycerol, and the like.

As another embodiment, the present invention provides a method for treating cancer and inhibiting cancer growth by administering the fusion protein or the composition containing the fusion protein of the present invention to a subject. The composition containing the fusion protein according to the present invention may be administered in a pharmaceutically effective amount in order to treat cancer cell or metastasis thereof or to inhibit cancer growth. The pharmaceutically effective amount may differ depending on various factors such as kinds of cancers, age and body weight of patient, feature and degree of symptoms, kinds of current therapy, treated frequency, formation and route to be administered, and may be easily determined by specialists in the corresponding art. The composition of the present invention may be simultaneously or sequentially administered with the above-described pharmacological or physiological components. In addition, the composition of the present invention may be administered in a combination of additional existing treatments and may be simultaneously or sequentially administered with the existing treatments. The administration may be a single or a multiple administration. It is important that the composition to be administered may be administered in the minimum amount providing the maximum effect without side-effects in consideration of all factors, wherein the amount may be easily determined by a person skilled in the art.

In the present invention, a term "subject" means a mammal suffering from a state or a disease capable of being reduced, inhibited, or treated by administering the fusion protein of the present invention or having a risk relevant thereto, and a human is preferred.

In the present invention, a term "administration" means an introduction of a predetermined material to a subject in any appropriate method, wherein the composition containing the fusion-protein of the present invention may be administered by any general route where the composition arrives at a desired tissue. Intraperitoneal administration, intravenous administration, intramuscular administration, subcutaneous administration, intradermal administration, oral administration, topical administration, intranasal administration, intrapulmonary administration, rectal administration may be included; however, the present invention is not limited thereto. However, since protein is digested in the case of oral administration, an oral composition is preferred to be provided by coating an active agent thereon or to be formulated so as to protect the composition from being digested in the stomach. In addition, the pharmaceutical composition may be administered by any apparatus in which an active agent is movable to a target cell.

Advantageous Effects

With the fusion protein according to the present invention, the cancer-specific antibody is linked to the angiogenesis inhibitor, and in particular, trastuzumab having excellent selective targeting of cancer cells or a fragment thereof are used as the cancer-specific antibody to thereby specifically function to the cancer cell, such that cancer cell proliferation may be inhibited and the angiogenesis surrounding cancer cells may be selectively inhibited, whereby the angiogenesis and the cancer growth may be inhibited even at low doses, high treatment effects against the cancer may be provided, and the side-effects may be remarkably decreased.

DESCRIPTION OF DRAWINGS

The above and other objects, features and advantages of the present invention will become apparent from the following description of preferred embodiments given in conjunction with the accompanying drawings, in which:

FIG. 1 represents an expression vector for expression of sc4D5-VT or VEGF-trap;

Figure 3:
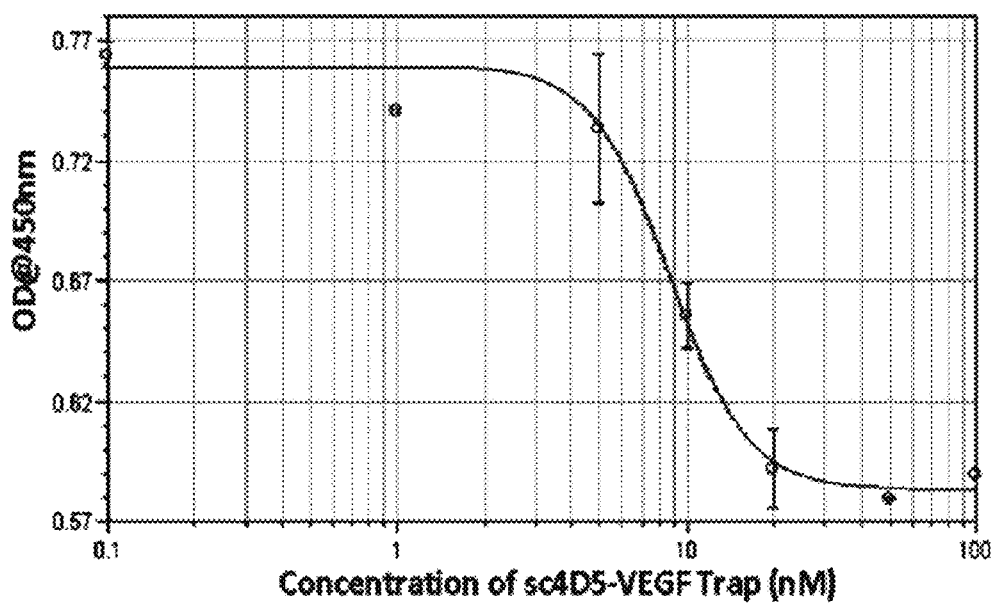
Figure 4:
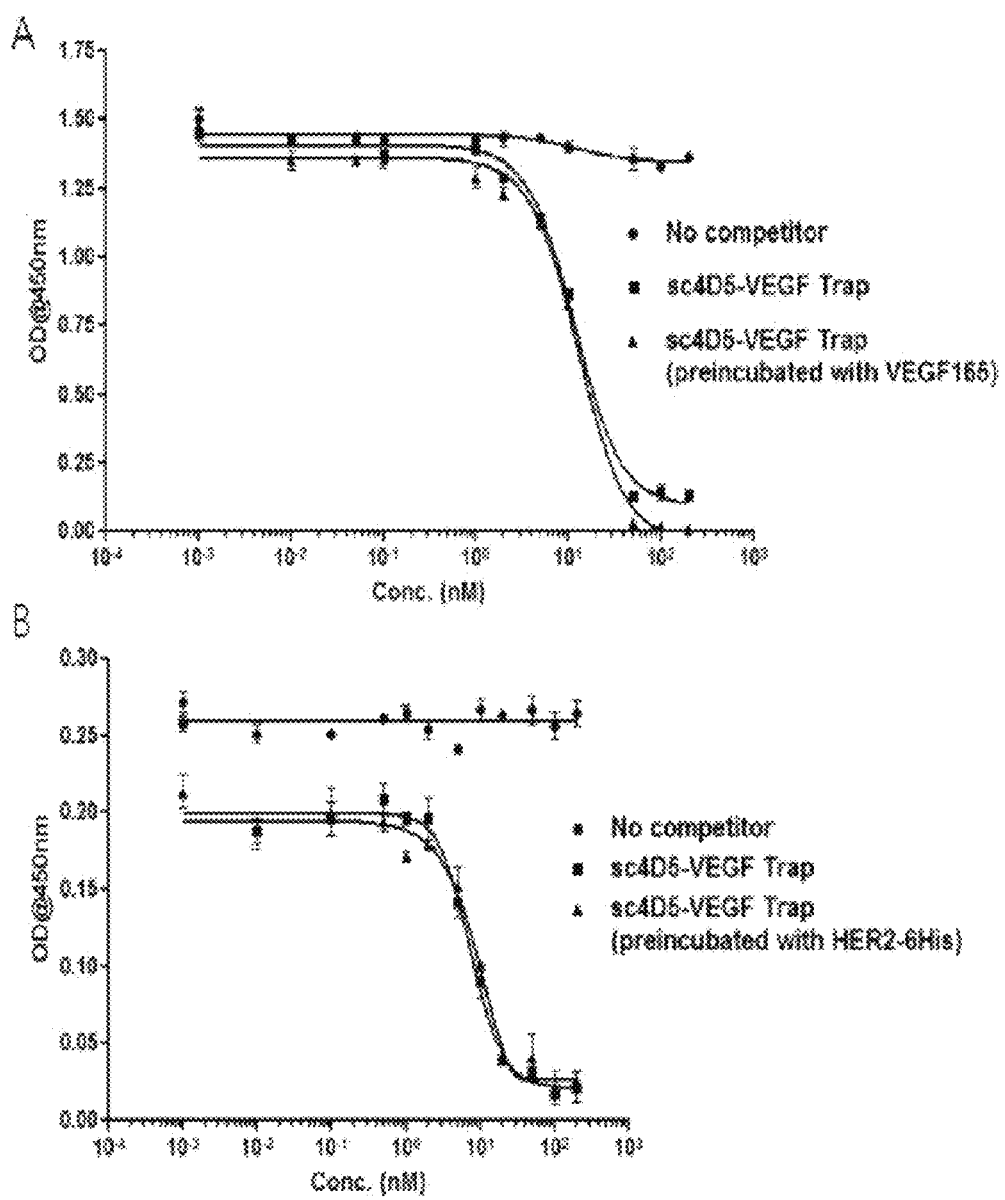
Figure 5:
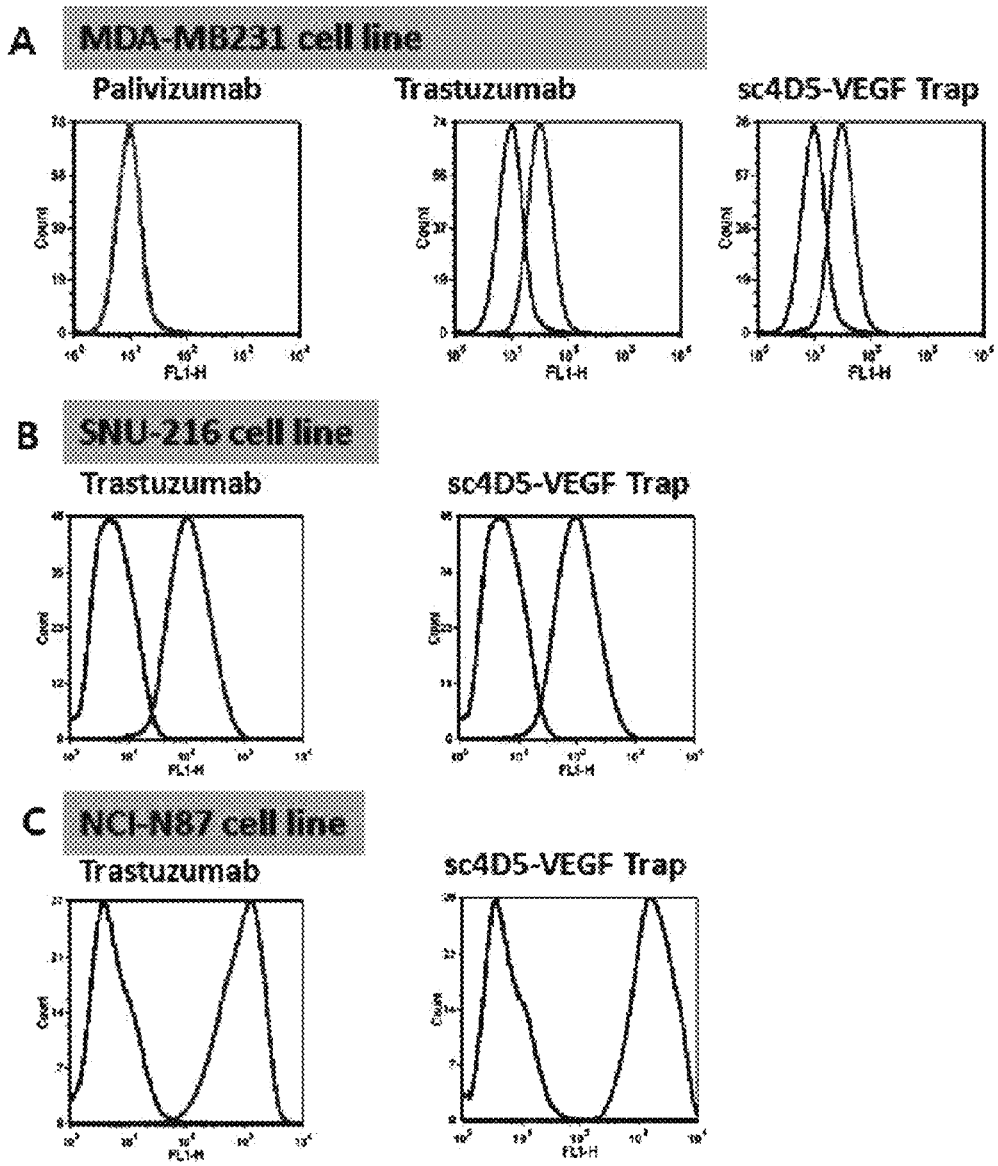
Figure 7:
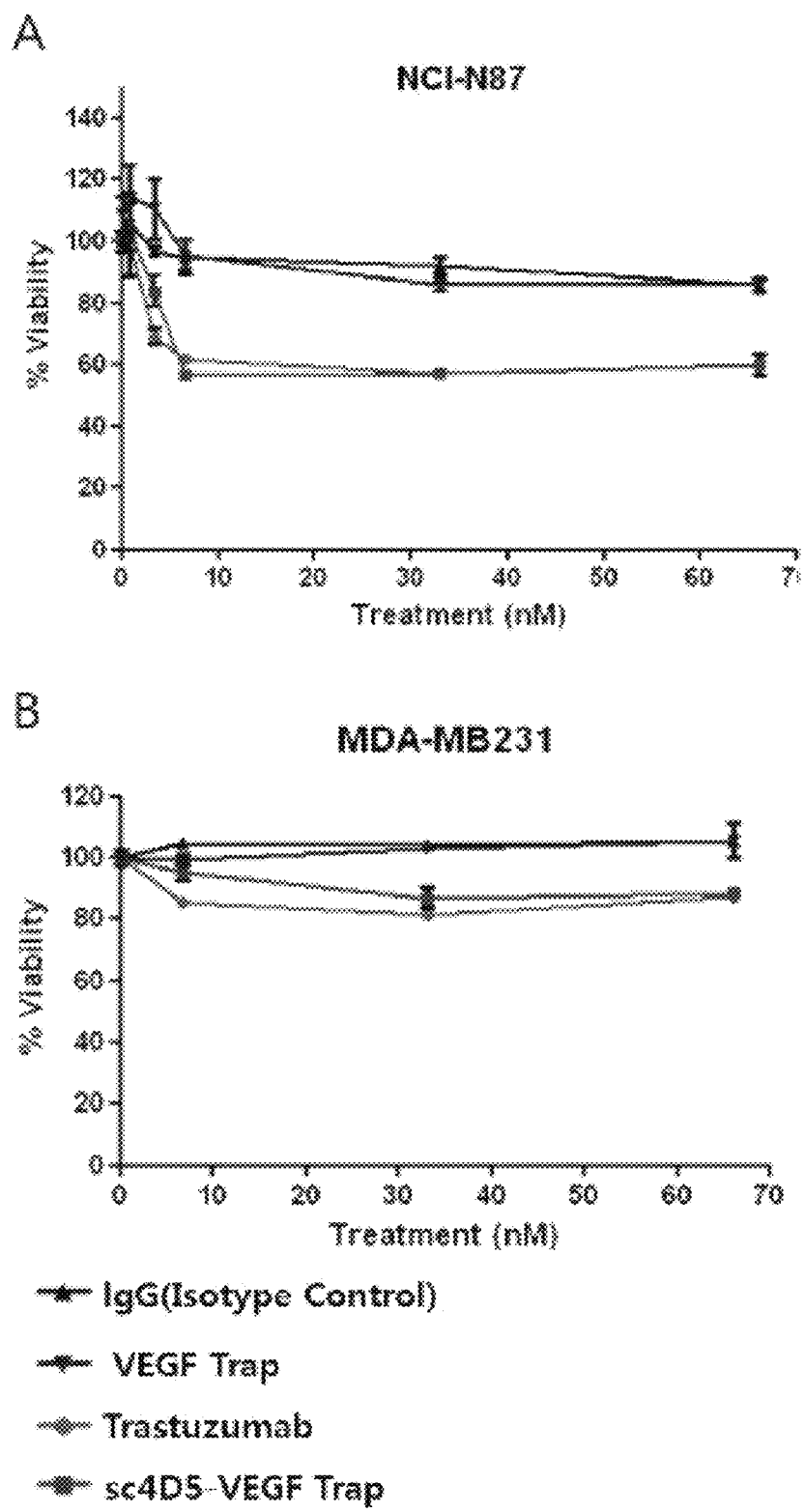
Figure 8:
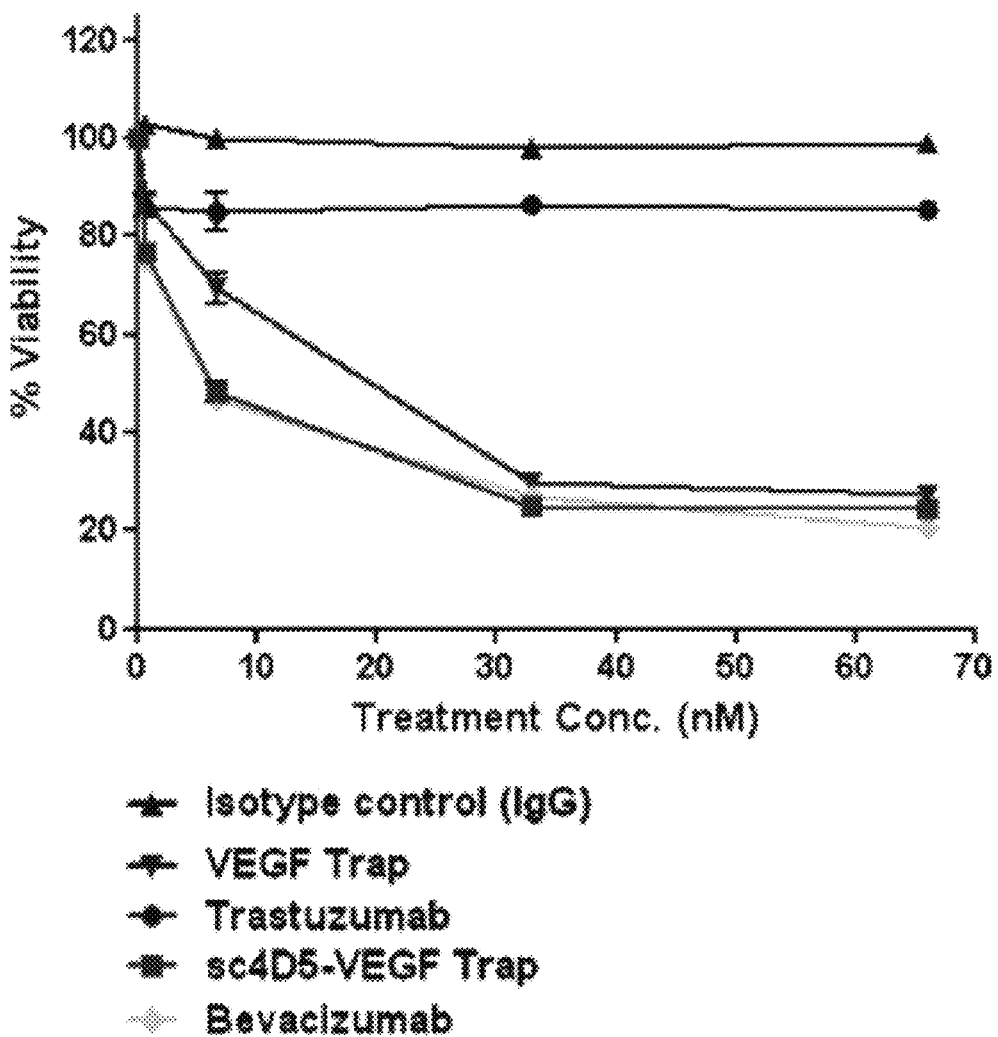
Figure 9:
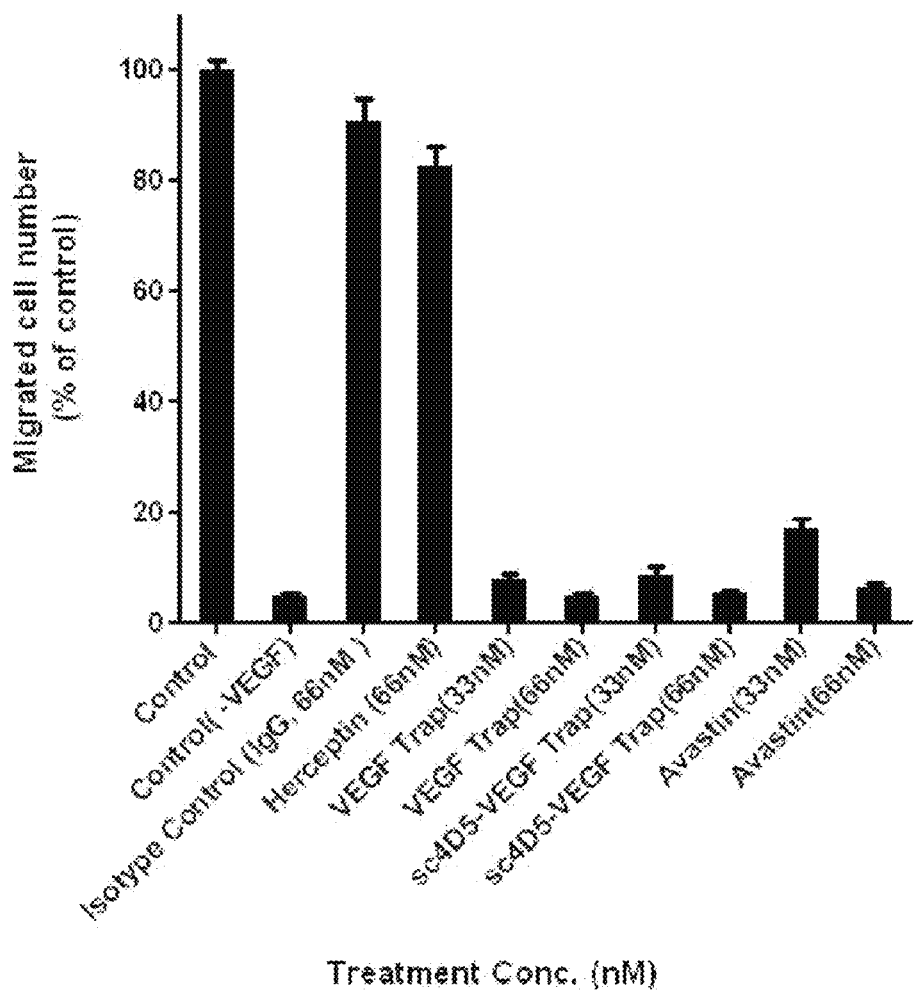
Figure 10:
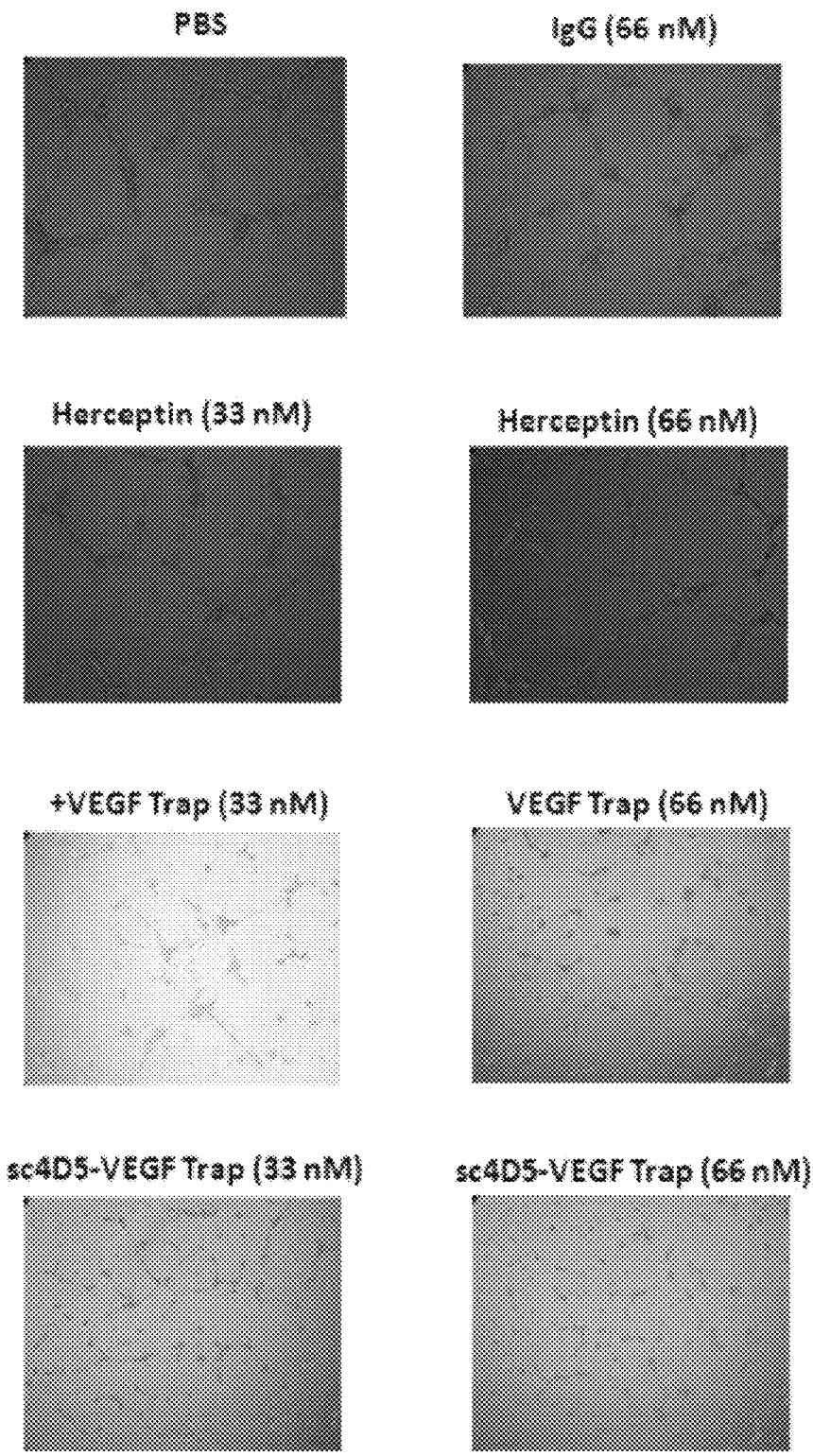
Figure 11:
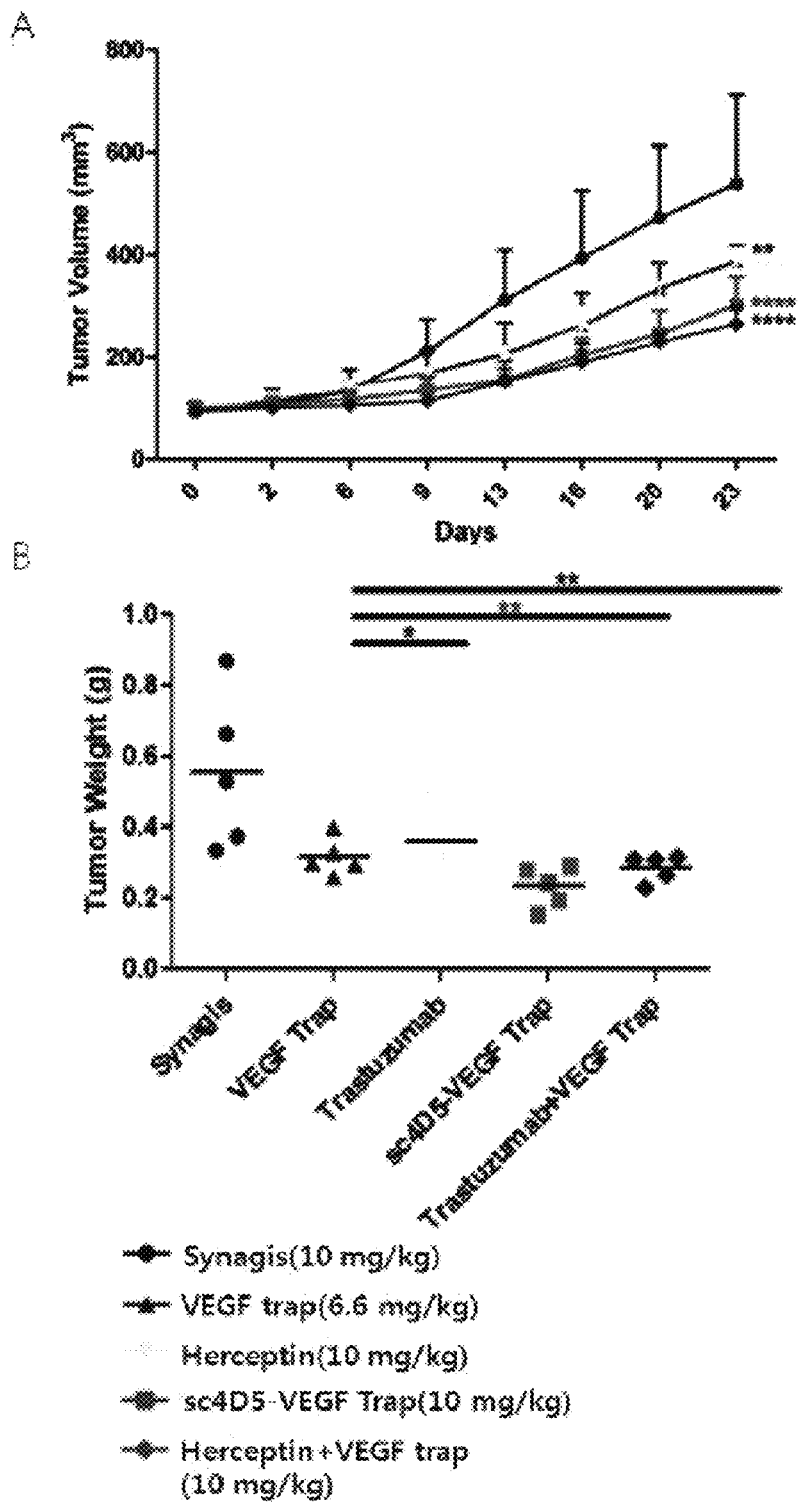
Figure 12:
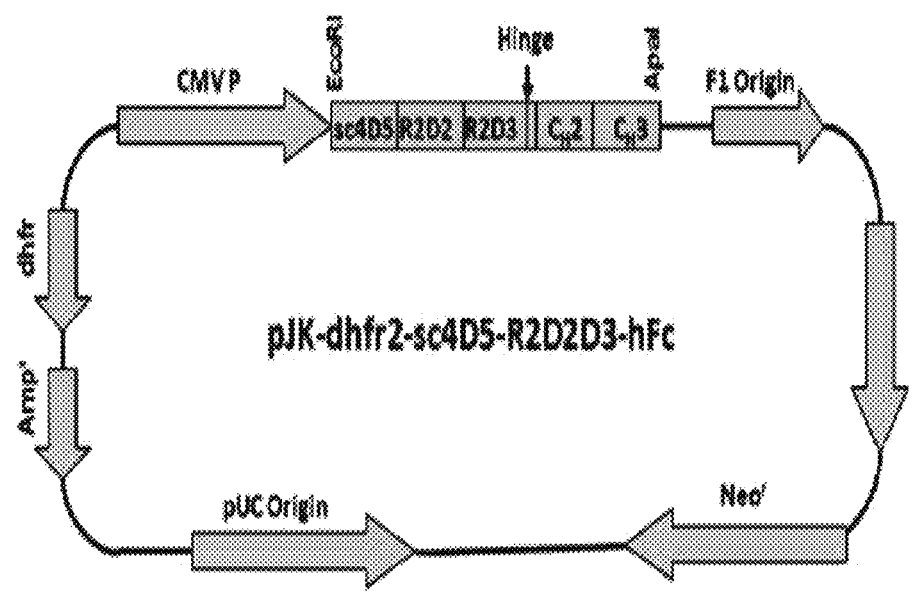
Figure 13:
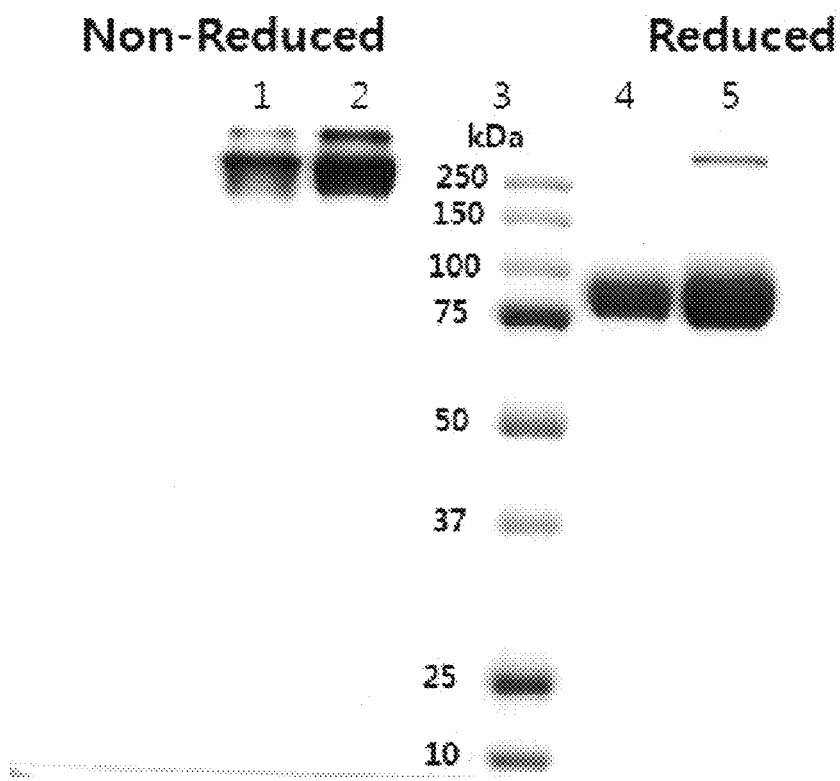
Figure 14:
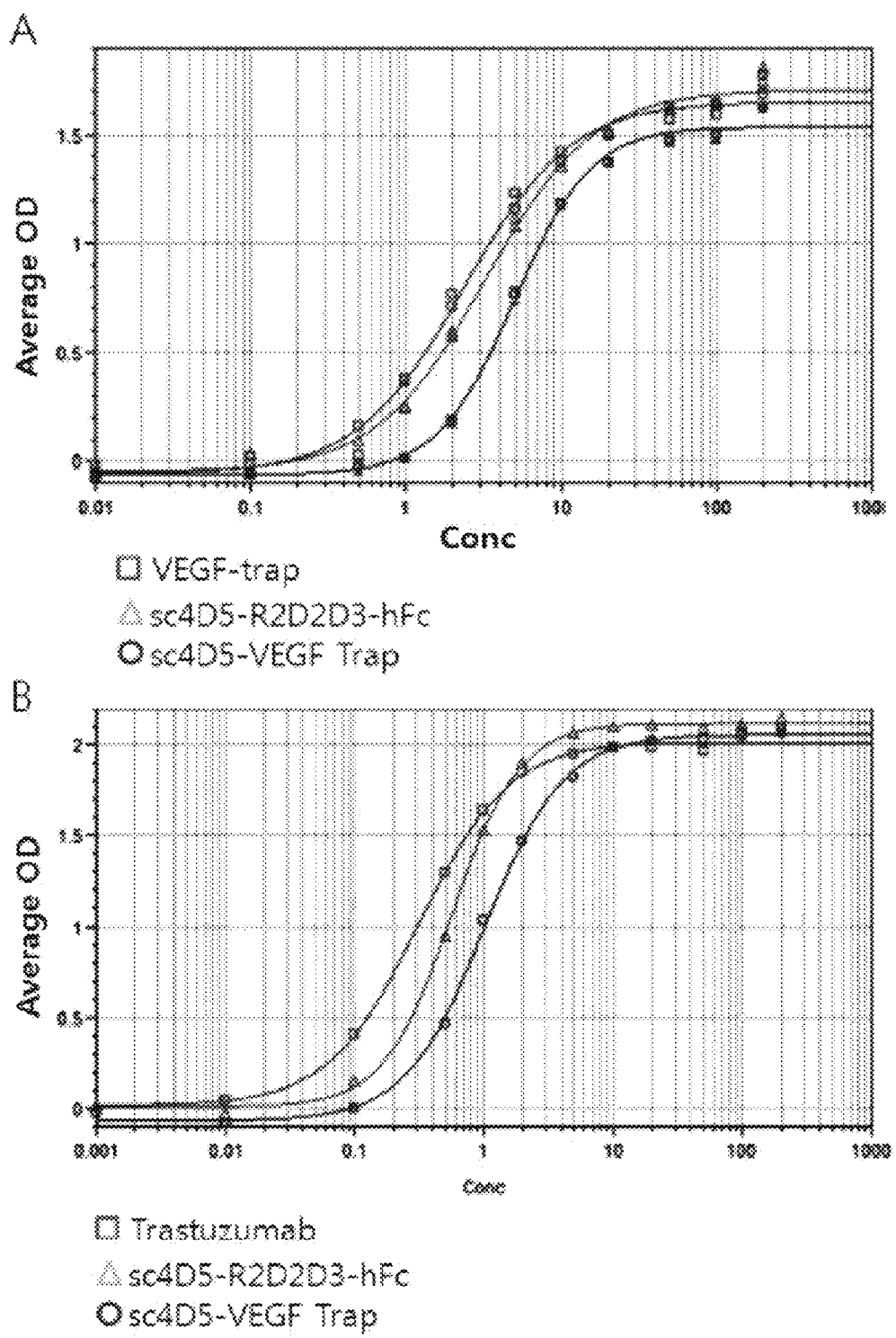

(A: Map of pJK-dhfr2-sc4D5-VEGF-Trap, B: Map of pJK-dhfr2-VEGF-Trap);

FIG. 2 shows a binding capacity of sc4D5-VT or VEGF-trap to VEGF;

(A: Binding capacity to VEGF-A, B: Binding capacity to VEGF-B);

FIG. 3 shows a binding capacity of sc4D5-VT to HER2/neu;

FIG. 4 shows that sc4D5-VT is simultaneously bound to HER2/neu and VEGF;

(A: binding capacity of sc4D5-VT bound to VEGF with respect to HER2/neu, B: binding capacity of sc4D5-VT bound to HER2/neu with respect to VEGF);

FIG. 5 shows whether or not HER2/neu is expressed on the surface of cancer cell lines such as MDA-MB231, SNU-216, and NCI-N87 cell;

FIG. 6 shows the results of cancer cell proliferation analysis by using a BrdU incorporation assay;

(A: NCI-N87 cell, B: MDA-MB231 cell);

FIG. 7 shows the results of cancer cell proliferation analysis by using a WST-1 method;

(A: NCI-N87 cell, B: MDA-MB231 cell);

FIG. 8 shows the results of cell proliferation analysis of human umbilical vein endothelial cells (HUVEC);

FIG. 9 shows the results of migration analysis of human umbilical vein endothelial cells (HUVEC);

FIG. 10 shows the results of tube formation analysis of human umbilical vein endothelial cells (HUVEC);

FIG. 11 shows the results of an animal study for in vivo anti-cancer activities in nude mice bearing NCI-N87 xenograft;

(A: result obtained by measuring a tumor size of NCI-N87 xenograft, B: result obtained by measuring a tumor weight of NCI-N87 xenograft);

FIG. 12 represents an expression vector for expression of sc4D5-R2D2D3-hFc;

FIG. 13 shows the result of SDS-PAGE of purified sc4D5-R2D2D3-hFc and sc4D5-VT;

FIG. 14 shows the binding capacity of sc4D5-R2D2D3-hFc or sc4D5-VT for VEGF165 or HER2/neu;

(A: binding capacity for VEGF165, B: binding capacity for HER2/neu); and

FIG. 15 shows that sc4D5-R2D2D3-hFc binds to VEGF165 and HER2/neu simultaneously.

BEST MODE

Hereinafter, embodiments of the present invention will be described through the following Examples in detail with reference to the accompanying drawings. However, this description is to help a specific understanding of the present invention, and a scope of the present invention is not limited to the following Examples.

Example 1

Preparation of sc4D5-VT Fusion Protein and VEGF-Trap Protein

In order to prepare a fusion protein (hereinafter, referred to as "sc4D5-VT") in which the N-terminus of VEGF-trap (Fc) 1 having an amino acid sequence described in SEQ. ID. NO: 1 is linked to the C-terminus of scFv (sc4D5) of trastuzumab having an amino acid sequence described in SEQ. ID. NO: 5 and having an amino acid sequence described in SEQ. ID. NO: 18, a vector was constructed as shown in FIG. 1A, and for comparison, a vector for producing only VEGF-trap was constructed as shown in FIG. 1B.

In the VEGF-trap (Fc) 1 having an amino acid sequence described in SEQ. ID. NO: 1 according to the present invention, domain 2 of VEGFR1, domain 3 of VEGFR2, hinge, and Fc regions ($C_H2$ and $C_H3$) of human IgG1 are sequentially linked to each other (U.S. Pat. No. 7,087,411). sc4D5 in FIG. 1A, which encodes scFv of trastuzumab, has a polynucleotide sequence described in SEQ. ID. NO: 8, and R1D2-R2D3-Hinge-CH2-CH3 in FIG. 1, which encodes VEGF-trap (Fc) 1, has a polynucleotide sequence described in SEQ. ID. NO: 9. Genes encoding sc4D5-VT and VEGF-trap (Fc) 1, respectively, were obtained from synthesis by Geneart Company in Germany. The synthesized sc4D5-VT or VEGF-trap (Fc) 1 gene was digested with EcoRI and ApaI, and subcloned into the EcoRI-ApaI sites of pJK-dhfr2 to obtain an expression vector: pJK-dhfr2-sc4D5-VEGF-Trap and pJK-dhfr2-VEGF-Trap.

In order to transfect HEK293T cells by using the expression vectors shown in FIGS. 1A and 1B, $2 \times 10^6$ cells were incubated in a 10 mm tissue culturing plate including Dulbecco's modified eagle's medium (DMEM) medium containing 10% fetal bovine serum (FBS) under 5% $CO_2$ atmosphere at 37° C. for 36 hours, and then a mixture of pJK-dhfr2-sc4D5-VEGF-Trap or pJK-dhfr2-VEGF-Trap DNA and PEI (Polyethylenimine, Polyscience, Inc., US) was added thereto. After 6 hours, the medium was replaced by CD293 (Invitrogen Corporation, US) which is a medium without protein. Supernatant was collected three times for every 72 hours, and protein was purified with Protein-A column (Pierce). After dialysis with PBS (pH 7.4), protein concentration was measured with a nanodrop. As a result, it could be appreciated that the fusion protein according to the present invention was normally expressed.

Example 2

Verification on Binding Capacity of sc4D5-VT to VEGF

In order to confirm that a binding capacity of sc4D5-VT to VEGF is maintained similar to VEGF-trap (Fc) 1, after 0.5 M carbonate bicarbonate buffer (pH 9.6) was used to coat VEGF-A and VEGF-B (R&D Systems) in 50 ng/well at 4° C. for 1 day in ELISA plate, the resultant was blocked with phosphate buffered saline (PBS) containing 2% skim milk at 37° C. for 1 hour, and sc4D5-VT and VEGF trap (Fc) 1 at various concentration were added thereto, respectively, and incubated for 1 hour. After washing, Goat Anti-human IgG (Fc-specific)-HRP (Pierce, US) diluted at a ratio of 1:5000 in PBST was added and incubated at 37° C. for 1 hour, then TMB (3,3',5,5'-Tetramethylbenzidine) as a substrate were added thereto, and OD was measured at 450 nm.

As a result, it could be appreciated that sc4D5-VT showed a binding capacity similar to VEGF-trap (Fc) 1 with respect to both of VEGF-A and VEGF-B (FIGS. 2A and 2B), and in the case in which VEGF-trap (Fc) 1 is bound to scFv fragment of trastuzumab, the binding capacity of VEGF-trap (Fc) 1 to VEGF and the biding property thereof were maintained.

Example 3

Verification on Binding Capacity of sc4D5-VT to HER2/neu

In order to confirm that a binding capacity of sc4D5-VT to HER2/neu is maintained, 0.5 M carbonate bicarbonate buffer (pH 9.6) was used to coat HER2/neu-Fc protein in 100 ng/well at 4° C. for 1 day in an ELISA trastuzumab plate. After the resultant was blocked with PBS containing 2% skim milk at 37° C. for 1 hour, trastuzumab and sc4D5-VT diluted in various concentrations were added into each well and incubated at 37° C. for 1 hour, followed by washing with PBS (PBST) containing 0.01% Tween-20 three times. Then, the resultant was incubated with Goat Anti-human IgG (Fab')$_2$—HRP (Pierce, US) diluted at a ratio of 1:5000 in PBST at 37° C. for 1 hour, TMB as a substrate was added thereto, and absorbance was measured at 450 nm.

As a result, sc4D5-VT effectively competed with trastuzumab in binding to HER2/neu-Fc in a dose-dependent manner (FIG. 3). The result indicates that the binding capacity of sc4D5-VT to HER2/neu was maintained (FIG. 3).

Example 4

Verification on Simultaneous Binding of sc4D5-VT to HER2/neu and VEGF

In order to confirm that one molecule of sc4D5-VT can bind to both of HER2/neu and VEGF, the following two competitive ELISAs were performed.

First, in order to analyze whether or not sc4D5-VT bound to VEGF has the same binding capacity to HER2/neu as free sc4D5-VT, trastuzumab was diluted with 0.5 M carbonate buffer (pH 9.6) and the diluted resultant of 0.5 μg was added to each well of ELISA plate and coated at 4° C. overnight. Then, plates were blocked with 1×PBS of 200 μl containing 2% skim milk (Difco) and 0.05% Tween 20 and washed with 0.05% PBST three times. After sc4D5-VT in various concentrations were preincubated with VEGF165(1 μg/ml of PBS, R&D Systems) or PBS at 37° C. for 1 hour, each resultant was mixed with Her2-6His (Sino biologicals) at a concentration of 100 ng/ml in PBS, followed by reaction at 37° C. for 2 hours. After the mixed solution was added to ELISA well having trastuzumab coated thereon, followed by reaction at 37° C. for 1 hour, anti-6H is-HRP (Abcam) of 100 μl diluted with PBS containing 0.05% Tween 20 at a ratio of 1/5,000 was added to the bound Her2-6H is, followed by reaction at 37° C. for 1 hour, TMB as a substrate was added thereto, and absorbance was measured at 450 nm.

As a result, it could be appreciated that sc4D5-VT having VEGF bound thereto and free sc4D5-VT inhibit the binding capacity of HER2-6H is to trastuzumab at the same level (FIG. 4A). The result demonstrated that sc4D5-VT bound to VEGF has the same binding capacity to HER2/neu as free sc4D5-VT.

Second, in order to analyze whether or not sc4D5-VT bound to HER2/neu has the same binding capacity to VEGF as free sc4D5-VT, VEGF trap (Fc) 1 was diluted with 0.5 M carbonate buffer (pH 9.6), and the diluted resultant of 0.5 μg was added to each well of ELISA plate and coated at 4° C. overnight. Then, the plates were blocked with 1×PBS of 200 μl containing 2% skim milk (Difco) and 0.05% Tween 20 and washed with 0.05% PBST three times. After sc4D5-VT in various concentrations were preincubated with Her2-6His (1 ug/ml of PBS) or PBS at 37° C. for 1 hour, each resultant was mixed with VEGF165 at a concentration of 100 ng/ml in PBS, followed by reaction at 37° C. for 2 hours. After the mixed solution was added to ELISA well having VEGF trap (Fc) 1 coated thereon, followed by reaction at 37° C. for 1 hour, anti-VEGF-HRP of 100 μl diluted with PBS containing 0.05%

Tween 20 at a ratio of 1/5,000 was added to the bound VEGF, followed by reaction at 37° C. for 1 hour, TMB as a substrate was added thereto, and absorbance was measured at 450 nm. The anti-VEGF-HRP was prepared by conjugating goat anti-human VEGF165 polyclonal antibody (R&D Systems) with HRP using EZ-Link Plus Activated Peroxidase kit (Thermo Scientific).

As a result, sc4D5-VT having Her2-6H is bound thereto and free sc4D5-VT inhibited the binding capacity of VEGF to VEGF trap (Fc) 1 at the same level (FIG. 4B). The result indicates that sc4D5-VT bound to HER2/neu has the same binding capacity to VEGF as free sc4D5-VT, suggesting that sc4D5-VT is capable of binding to HER2/neu and VEGF simultaneously.

Example 5

Confirmation of Cancer Cell Proliferation Inhibition by sc4D5-VT

As shown in the results of Examples 2 through 4 above, sc4D5-VT has binding capacity to VEGF and HER2/neu. To analyze whether or not sc4D5-VT can bind to the surface of a cell expressing Her2, flow cytometric analysis was performed. More specifically, breast cancer cell line MDA-MB231(ATCC HTB-26) and stomach cancer cell lines SNU-216(ATCC CRL-5974) and NCI-N87 (ATCC CRL-5822) were used, and as primary antibodies, Palivizumab (Synagis) which is a humanized antibody to respiratory syncytial virus (RSV) was used as a negative control, and trastuzumab was used as a positive control, and as secondary antibodies, goat anti-human IgG(Fc)-FITC conjugate (Sigma, US) was used. The cells were dissociated using cell dissociation enzyme-free Hank's-based buffer (Invitrogen Corporation, US), resuspended in PBA (PBS including 3% BSA and 0.09% $NaN_3$ added thereto) at $2 \times 10^5$ cells/ml concentration, and fixed with 0.01% formaldehyde for 15 minutes. After the primary antibodies were incubated with the cells at 4° C. for 20 minutes, the secondary antibodies were added and incubated at 4° C. for 20 minutes. Then the cells were analyzed by flow cytometry.

As a result, as shown in FIG. 5, trastuzumab used as a positive control weakly bound to MDA-MB231, moderately bound to SNU-216, and strongly bound to NCI-N87 cells. The results indicate that cell surface expression level of Her2 is increased in MDA-MB231, SNU-216, and NCI-N87 cells in order. sc4D5-VT showed the same binding capacity as trastuzumab to the cell lines. Therefore, NCI-N87 cells having a high expression level of Her2 were used to analyze the antitumor efficacy of sc4D5-VT, while a MDA-MB231 cell having a low expression level of Her2 was used as a negative control.

In particular, since it was reported that treatment of Her2-overexpressing cancer cells with trastuzumab resulted in decrease in cell division (Gong et al., 2004, Cancer Lett. 214(2): 215-24), bromodeoxyuridine incorporation (BrdU Incorporation) method was used to analyze a stomach cancer cell proliferation inhibition effect by sc4D5-VT. More specifically, NCI-N87 cells and MDA-MB231 cells were incubated in RPMI 1640 (Gibco) medium or DMEM medium containing 10% FBS, respectively, and at the time of 80% confluency, sc4D5-VT, trastuzumab, VEGF-trap (Fc) 1 at 33 nM or 66 nM concentration, or PBS as a negative control were added thereto, followed by incubation for 48 hours. Then, 10 μM BrdU was added thereto and the resultant was incubated for 6 hours. Cells were dissociated with trypsin and stained using APC BrdU Flow Kit (BD Pharmingen, US), and flow cytometry using BD FACS caliber (BD Bioscience, US) was performed to measure the number of BrdU incorporated cells.

As a result, as shown in FIG. 6A, sc4D5-VT or trastuzumab inhibited proliferation of NCI-N87 cells that express high level of Her2, whereas VEGF-trap (Fc) 1 did not. In contrast, sc4D5-VT or trastuzumab did not inhibit proliferation of MDA-MB231 cells with low level of Her2 expression (FIG. 6B).

In addition, a WST-1 assay was performed to analyze the cell proliferation inhibition. To this end, cells were divided by $5 \times 10^3$ cells for each well of a 96-well plate and incubated under 5% $CO_2$ atmosphere at 37° C. for 24 hours, and antibody samples or PBS in various concentrations were added thereto, followed by incubation for 72 hours. After a WST-1 solution (Roche Applied Science, US) of 10 μl was added to each well, followed by incubation at 37° C. for 4 hours, absorbance was measured at 410 nm with a reference of 610 nm. Viability (%) is a value showing a ratio of viability in cells using PBS based on 100%.

As a result, sc4D5-VT or trastuzumab inhibited the cell proliferation by the maximum of about 40%; however, VEGF-trap (Fc) 1 or IgG as a negative control did not inhibit the cell proliferation (FIG. 7A). Meanwhile, MDA-MB231 cell proliferation was not inhibited by sc4D5-VT or trastuzumab (FIG. 7B).

The above-described results suggest that sc4D5-VT could effectively inhibit proliferation of stomach cancer cells expressing high level of Her2 and thus be useful for the treatment of the cancer, like trastuzumab.

Example 6

Inhibition of Angiogenesis by sc4D5-VT

In order to confirm whether or not sc4D5-VT inhibits angiogenesis, proliferation, migration, and differentiation assays of human umbilical vein endothelial cells (HUVEC) were performed.

(1) Proliferation Inhibition of HUVEC by sc4D5-VT

After 10,000 HUVEC were added to 100 μl of EBM-2 medium (Lonza, Switzerland), EBM-2 medium having VEGF-A (50 ng/ml) was added thereto, or EBM-2 medium including VEGF-A (50 ng/ml) and antibody sample at different concentration was added thereto in each well of a 96-well plate, followed by incubation under 5% $CO_2$, at 37° C. for 72 hours. Then, 10 μl of WST-1 solution was added thereto, followed by incubation at 37° C. for 4 hours. Absorbance was measured at 410 nm with a reference of 610 nm.

As a result, as shown in FIG. 8, VEGF-trap (Fc) 1, sc4D5-VT, or bevacizumab (Avastin) which is VEGF neutralizing antibody inhibited proliferation of HUVEC, whereas trastuzumab or IgG as a negative control did not.

(2) Migration Inhibition of HUVEC by sc4D5-VT

After a bottom of Transwells, (Corning Inc., US) having a pore size of 8-μm was coated with 0.1% gelatin and mounted in a 24-well plate, a lower chamber was filled with 600 μl of EBM-2 medium (Lonza), EBM-2 with VEGF-A (50 ng/ml), or EBM-2 with VEGF-A (50 ng/ml) and antibody sample at different concentration. An upper chamber was provided with 100 μl of EBM-2 medium containing $1 \times 10^5$ HUVEC. After incubation in 37° C. cell incubator for 4 hours, a filter was detached from the Transwell and cells were fixed with methanol for 1 minute and stained with Hematoxylin/Eosin. Cells which did not migrate but were left on an upper surface of the transwell were completely removed with a cotton swab. Five random fields among the cells migrated through the filter were arbitrarily chosen under an optical microscope (×100) and the number thereof was counted.

As a result, as shown in FIG. 9, trastuzumab did not inhibit migration of HUVEC; however, VEGF-trap (Fc) 1, sc4D5-VT, or bevacizumab which is a VEGF neutralizing antibody inhibited migration of HUVEC.

(3) Inhibition of Tube Formation by sc4D5-VT

In order to confirm that sc4D5-VT can inhibit differentiation of HUVEC, tube formation assay was performed.

More specifically, after a 96-well plate was coated with Growth Factor Reduced Matrigel (BD Biosciences, US), 15,000 HUVEC in 100 μl of EBM-2 medium, EBM-2 medium with VEGF-A (50 ng/ml), or EBM-2 medium with VEGF-A (50 ng/ml) and an antibody sample were added to each well, followed by incubation in 37° C. cell incubator for 6 hours. Then, tube formation was observed by using an inverted microscope.

As a result, as shown in FIG. 10, trastuzumab did not inhibit differentiation of HUVEC; however, VEGF-trap (Fc) 1 or sc4D5-VT inhibited the tube formation of HUVEC.

Results from the example 5 and the example 6 are summarized in the following Table 1.

TABLE 1

Inhibition of Cancer Cell Proliferation and Angiogenesis by Each Protein

| Classification | Inhibition of Cancer Cell Proliferation | Inhibition of Angiogenesis |
|---|---|---|
| Sc4D5-VT | + | + |
| Trastuzumab | + | − |
| VEGF Trap (Fc) 1 | − | + |

As described above, sc4D5-VT inhibited both stomach cancer cell proliferation and angiogenesis, and therefore may exert a higher antitumor efficacy as compared to that of trastuzumab or VEGF-trap (Fc) 1.

Example 7

Animal Study of sc4D5-VT, VEGF Trap (Fc) 1, and Trastuzumab

In order to compare in vivo anti-tumor efficacy of sc4D5-VT with that of VEGF Trap (Fc) 1 or that of trastuzumab, sc4D5-VT and VEGF-trap (Fc) 1 were expressed and purified as described in Example 1. As Agilent 2100 Bioanalyzer (Agilent Technologies) was used to measure purity of the purified protein, purity of sc4D5-VT and VEGF-trap (Fc) 1 was 93.3% and 96.8%, respectively. As endotoxin content of the purified sc4D5-VT or VEGF-trap (Fc) 1 (1 mg/ml) was measured by Lumulus Amebocyte Lysate Kit (Lonza), the content was less than 0.25 EU/ml, which indicates no endotoxin contamination in the purified protein. The purified sc4D5-VT or VEGF-trap (Fc) 1 was used for animal study.

NCI-N87 cells ($5 \times 10^6$) were subcutaneously injected into BALB/c Slc-nu nude mouse (Japan SLC, Inc.) and after 7 days tumor volume (about 90 mm$^3$) was measured. Synagis as an isotype control (66.66 nM/kg of body weight), VEGF-trap (Fc) 1 (66.66 nM/kg of body weight), trastuzumab (66.66 nM/kg), sc4D5-VT (66.66 nM/kg), or a mixture of VEGF-trap (Fc) 1 (66.66 nM/kg) and trastuzumab (66.66 nM/kg) were intravenously injected into each of the 7 mice per group three times a week for four weeks. Tumor volume was measured (Volume=a×b$^2$/2, a=width at the widest point of tumor, b=width perpendicular to a) using calipers twice per week.

As a result, as shown in FIG. 11, sc4D5-VT showed greater inhibition of the tumor growth compared with VEGF trap (Fc) 1 or trastuzumab, and the efficacy was similar to that of combination treatment of VEGF trap (Fc) 1 and trastuzumab having the same concentration.

Example 8

Production of sc4D5-R2D2D3-hFc and Efficacy Confirmation

In order to produce sc4D5-R2D2D3-hFc including domain 2-domain 3 (R2D2D3) of receptor VEGFR2, which is another form (VEGF-trap (Fc) 2) of VEGF-trap (Fc), and having an amino acid sequence described in SEQ. ID. NO: 12, the gene encoding sc4D5-R2D2D3-hFc was synthesized by Geneart Company in Germany. The synthesized gene was digested with EcoRI and ApaI and subcloned into the EcoRI-ApaI sites of pJK-dhfr2-sc4D5-VEGF-Trap of Example 1 to obtain an expression plasmid: pJK-dhfr2-sc4D5-R2D2D3-hFc (FIG. 12). As described in Example 1, pJK-dhfr2-sc4D5-R2D2D3-hFc was introduced into HEK293T cell to express sc4D5-R2D2D3-hFc, and the expressed protein was purified from the culture supernatant by using Protein-A column. Purified sc4D5-R2D2D3-hFc was analyzed by 10% SDS-PAGE (FIG. 13).

In order to confirm a binding activity of sc4D5-R2D2D3-hFc for VEGF, sc4D5-VT, VEGF trap (Fc) 2, and sc4D5-R2D2D3-hFc were analyzed by an indirect ELISA using VEGF165 as described in Example 2 above. As a result, the binding activities of sc4D5-R2D2D3-hFc, sc4D5-VT, and VEGF trap (Fc) 2 were not much different from each other (FIG. 14A).

In order to confirm a binding activity of sc4D5-R2D2D3-hFc for HER2/neu, sc4D5-VT, VEGF trap (Fc) 2, and sc4D5-R2D2D3-hFc were analyzed by an indirect ELISA as described in Example 3 above. As a result, the binding activities of sc4D5-VT, VEGF trap (Fc) 2 and sc4D5-R2D2D3-hFc were not much different from each other (FIG. 14B).

Example 9

Verification on Simultaneous Binding of sc4D5-R2D2D3-hFc to HER2/neu and VEGF

In order to confirm that sc4D5-R2D2D3-hFc is capable of binding to both HER2/neu and VEGF simultaneously, a competitive ELISA was performed.

in order to analyze whether or not sc4D5-R2D2D3-hFc bound to HER2/neu has the same binding capacity to VEGF as free sc4D5-R2D2D3-hFc, VEGF trap (Fc) 1 was diluted with 0.5 M carbonate buffer (pH 9.6), and the diluted resultant of 0.5 µg was added to each well of ELISA plate and coated at 4° C. overnight. Then, the plates were blocked with 1×PBS of 200 µl containing 2% skim milk (Difco) and 0.05% Tween 20 and washed with 0.05% PBST three times. After sc4D5-R2D2D3-hFc in various concentrations were preincubated with Her2-6His (1 ug/ml of PBS) or PBS at 37° C. for 1 hour, each resultant was mixed with VEGF165 at a concentration of 100 ng/ml in PBS, followed by reaction at 37° C. for 2 hours. After the mixed solution was added to ELISA well having VEGF trap (Fc) 1 coated thereon, followed by reaction at 37° C. for 1 hour, anti-VEGF-HRP of 100 µl diluted with PBS containing 0.05% Tween 20 at a ratio of 1/5,000 was added to the bound VEGF, followed by reaction at 37° C. for 1 hour, TMB as a substrate was added thereto, and absorbance was measured at 450 nm. The anti-VEGF-HRP was prepared as described in Example 4 above.

As a result, the sc4D5-R2D2D3-hFc having Her2-6H is bound thereto and free sc4D5-R2D2D3-hFc inhibited the binding capacity of VEGF to VEGF trap (Fc) 1 at the same level (FIG. 15). The result indicates that sc4D5-R2D2D3-hFc bound to HER2/neu has the same binding capacity to VEGF as free sc4D5-R2D2D3-hFc, suggesting that sc4D5-R2D2D3-hFc is capable of binding to HER2/neu and VEGF simultaneously.

SEQUENCE LISTING FREE TEXT

SEQ. ID. NO: 1 is an amino acid sequence of VEGF-trap (Fc) 1.
SEQ. ID. NO: 2 is an amino acid sequence of a heavy chain variable region of scFv of trastuzumab.
SEQ. ID. NO: 3 is an amino acid sequence of a light chain variable region of scFv of trastuzumab.
SEQ. ID. NO: 4 is an amino acid sequence of linker between VH and VL.
SEQ. ID. NO: 5 is an amino acid sequence of scFv of trastuzumab.
SEQ. ID. NO: 6 is an amino acid sequence of a sc4D5-VEGF-trap 1 fusion protein.
SEQ. ID. NO: 7 is an amino acid sequence of a leader peptide.
SEQ. ID. NO: 8 is a polynucleotide sequence encoding scFv of trastuzumab.
SEQ. ID. NO: 9 is a polynucleotide sequence encoding VEGF-trap (Fc) 1.
SEQ. ID. NO: 10 is a polynucleotide sequence encoding sc4D5-VEGF-trap (Fc) 1 fusion protein.
SEQ. ID. NO: 11 is a polynucleotide sequence encoding a leader peptide.
SEQ. ID. NO: 12 is an amino acid sequence of VEGF-trap (Fc) 2.
SEQ. ID. NO: 13 is an amino acid sequence of VEGF-trap 1.
SEQ. ID. NO: 14 is an amino acid sequence of VEGF-trap 2.
SEQ. ID. NO: 15 is an amino acid sequence of Human Fc.
SEQ. ID. NO: 16 is a polynucleotide sequence encoding VEGF-trap (Fc) 2.
SEQ. ID. NO: 17 is a polynucleotide sequence encoding VEGF-trap 1.
SEQ. ID. NO: 18 is the entire amino acid sequence of a sc4D5-VEGF-trap (Fc) 1 fusion protein.
SEQ. ID. NO: 19 is a polynucleotide sequence encoding VEGF-trap 2.
SEQ. ID. NO: 20 is a polynucleotide sequence encoding a sc4D5-VEGF-trap 1 fusion protein.
SEQ. ID. NO: 21 is the entire amino acid sequence of a sc4D5-VEGF-trap 2 fusion protein.
SEQ. ID. NO: 22 is a polynucleotide sequence encoding a sc4D5-VEGF-trap 2 fusion protein.
SEQ. ID. NO: 23 is the entire amino acid sequence of a sc4D5-VEGF-trap (Fc) 2 fusion protein.
SEQ. ID. NO: 24 is a polynucleotide sequence encoding a sc4D5-VEGF-trap (Fc) 2 fusion protein.

The invention claimed is:

1. A fusion protein which binds HER2 or a fragment thereof, said fusion protein comprising:

a vascular endothelial growth factor VEFG-trap of the amino acid sequence of SEQ ID NO: 1; and a scFv of trastuzumab, said scFv has the amino acid sequence of SEQ ID NO: 5.

2. The fusion protein of claim 1, wherein the N-terminus of the VEFG-trap is linked to the C-terminus of the scFv of trastuzumab.

3. The fusion protein of claim 1, wherein the fusion protein has the amino acid sequence of SEQ ID NO: 18.

* * * * *